United States Patent
Smith et al.

(10) Patent No.: US 12,230,380 B2
(45) Date of Patent: Feb. 18, 2025

(54) MACHINE LEARNING TECHNIQUES FOR PROSPECTIVE EVENT-BASED CLASSIFICATION

(71) Applicant: UnitedHealth Group Incorporated, Minnetonka, MN (US)

(72) Inventors: Jeffrey Smith, Prior Lake, MN (US); Marissa N. Dent, Homer Glen, IL (US); Louis A. Wedge, Stillwater, MN (US); Cary R. Shelley, Catonsville, MD (US); Aliya Mansoor, Columbia, MD (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 312 days.

(21) Appl. No.: 17/651,873

(22) Filed: Feb. 21, 2022

(65) Prior Publication Data

US 2023/0086384 A1    Mar. 23, 2023

Related U.S. Application Data

(60) Provisional application No. 63/261,496, filed on Sep. 22, 2021.

(51) Int. Cl.
*G06F 18/2431* (2023.01)
*G16H 20/10* (2018.01)

(52) U.S. Cl.
CPC ......... *G16H 20/10* (2018.01); *G06F 18/2431* (2023.01)

(58) Field of Classification Search
CPC ........................... G16H 20/10; G06F 18/2431
See application file for complete search history.

(56) References Cited

U.S. PATENT DOCUMENTS

| | | | |
|---|---|---|---|
| 8,265,954 | B2 | 9/2012 | Hasan et al. |
| 8,428,966 | B2 | 4/2013 | Green, III et al. |
| 8,909,593 | B2 | 12/2014 | Patel et al. |
| 9,710,600 | B1 | 7/2017 | Dunleavy et al. |
| 10,170,203 | B1 | 1/2019 | Blechman |
| 10,276,263 | B2 | 4/2019 | Connely et al. |

(Continued)

FOREIGN PATENT DOCUMENTS

| | | |
|---|---|---|
| GB | 2385971 A | 9/2003 |
| WO | 02/52483 A2 | 7/2002 |

(Continued)

OTHER PUBLICATIONS

Final Office Action for U.S. Appl. No. 16/689,288, dated Sep. 6, 2022, (21 pages), United States Patent and Trademark Office, US.

(Continued)

*Primary Examiner* — Raquel Alvarez
(74) *Attorney, Agent, or Firm* — ALSTON & BIRD LLP

(57) ABSTRACT

Various embodiments of the present invention provide methods, apparatus, systems, computing devices, computing entities, and/or the like for performing predictive data analysis. Certain embodiments of the present invention utilize systems, methods, and computer program products that perform predictive data analysis by using at least one of prospective coverage score determination machine learning models and prospective event-based classification machine learning models.

20 Claims, 8 Drawing Sheets

(56) References Cited

U.S. PATENT DOCUMENTS

| | | |
|---|---|---|
| 10,296,715 B1 | 5/2019 | Smith et al. |
| 10,586,615 B2 | 3/2020 | Bastide et al. |
| 10,742,654 B1 | 8/2020 | Pinsonneault et al. |
| 10,799,189 B2 | 10/2020 | Nye et al. |
| 10,990,352 B1 | 4/2021 | Artz et al. |
| 11,031,109 B2 | 6/2021 | Devarakonda et al. |
| 11,101,026 B2 | 8/2021 | Francois et al. |
| 11,120,906 B2 | 9/2021 | Gandy et al. |
| 11,392,669 B1 | 7/2022 | Jaladi et al. |
| 11,830,584 B2 | 11/2023 | Hansen et al. |
| 2002/0083075 A1 | 6/2002 | Brummel et al. |
| 2003/0191669 A1 | 10/2003 | Fitzgerald et al. |
| 2004/0111296 A1 | 6/2004 | Rosenfeld et al. |
| 2007/0162308 A1 | 7/2007 | Peters |
| 2009/0254368 A1 | 10/2009 | Cunnold |
| 2009/0271218 A1 | 10/2009 | Mok et al. |
| 2011/0099027 A1 | 4/2011 | Weathers |
| 2011/0106564 A1 | 5/2011 | Hachmeister et al. |
| 2011/0191822 A1 | 8/2011 | Pinsky et al. |
| 2012/0129139 A1 | 5/2012 | Partovi |
| 2012/0166226 A1 | 6/2012 | Lee et al. |
| 2012/0271612 A1 | 10/2012 | Barsoum et al. |
| 2013/0054264 A1 | 2/2013 | Baronov et al. |
| 2013/0085779 A1 | 4/2013 | Vilsmeier |
| 2013/0096938 A1 | 4/2013 | Stueckemann et al. |
| 2013/0110755 A1 | 5/2013 | Upadhyayula et al. |
| 2013/0179189 A1 | 7/2013 | Brown |
| 2013/0191135 A1 | 7/2013 | Camacho et al. |
| 2013/0191157 A1 | 7/2013 | Eiden et al. |
| 2013/0332194 A1 | 12/2013 | D'Auria et al. |
| 2014/0039911 A1 | 2/2014 | Iyer |
| 2014/0058742 A1 | 2/2014 | Chari et al. |
| 2014/0136233 A1 | 5/2014 | Atkinson et al. |
| 2014/0236630 A1 | 8/2014 | Murata |
| 2014/0278534 A1 | 9/2014 | Romeo |
| 2014/0372141 A1 | 12/2014 | Renner et al. |
| 2015/0019248 A1 | 1/2015 | Anand et al. |
| 2015/0039343 A1 | 2/2015 | Cline et al. |
| 2015/0046173 A1 | 2/2015 | Furletti et al. |
| 2015/0066539 A1 | 3/2015 | Sheffer et al. |
| 2015/0081332 A1 | 3/2015 | Casper et al. |
| 2015/0213195 A1 | 7/2015 | Blechman |
| 2015/0242955 A1 | 8/2015 | Long et al. |
| 2015/0294089 A1 | 10/2015 | Nichols |
| 2015/0347705 A1 | 12/2015 | Simon et al. |
| 2015/0363555 A1 | 12/2015 | Studsrud |
| 2016/0012187 A1 | 1/2016 | Zasowski et al. |
| 2016/0019352 A1 | 1/2016 | Cohen et al. |
| 2016/0055314 A1 | 2/2016 | Anderson et al. |
| 2016/0125550 A1 | 5/2016 | Joao et al. |
| 2016/0180030 A1 | 6/2016 | Gunawardena et al. |
| 2016/0253687 A1 | 9/2016 | Wei et al. |
| 2016/0267223 A1 | 9/2016 | Allen et al. |
| 2016/0285876 A1 | 9/2016 | Perez et al. |
| 2016/0357910 A1 | 12/2016 | Ghouri et al. |
| 2016/0357915 A1 | 12/2016 | Morris et al. |
| 2016/0357932 A1 | 12/2016 | Morris et al. |
| 2016/0358288 A1 | 12/2016 | McKenzie et al. |
| 2017/0076046 A1 | 3/2017 | Barnes et al. |
| 2017/0109478 A1 | 4/2017 | Hasan et al. |
| 2017/0161435 A1 | 6/2017 | Orosco et al. |
| 2017/0161439 A1 | 6/2017 | Raduchel et al. |
| 2017/0262604 A1 | 9/2017 | Francois |
| 2017/0300647 A1 | 10/2017 | Goldberg et al. |
| 2017/0372430 A1 | 12/2017 | Maddison et al. |
| 2018/0046764 A1 | 2/2018 | Katwala et al. |
| 2018/0102190 A1 | 4/2018 | Hogue et al. |
| 2018/0121843 A1 | 5/2018 | Connely, IV et al. |
| 2018/0181720 A1 | 6/2018 | Ensey et al. |
| 2018/0286509 A1 | 10/2018 | Shah et al. |
| 2018/0350461 A1 | 12/2018 | Anderson |
| 2019/0096534 A1 | 3/2019 | Joao |
| 2019/0208354 A1 | 7/2019 | Raduchel et al. |
| 2019/0244683 A1 | 8/2019 | Francois |
| 2019/0267143 A1 | 8/2019 | Sikander et al. |
| 2019/0279753 A1 | 9/2019 | Rourke et al. |
| 2020/0160955 A1 | 5/2020 | Hansen et al. |
| 2020/0167879 A1 | 5/2020 | Patel et al. |
| 2020/0176089 A1 | 6/2020 | Jones et al. |
| 2020/0342969 A1 | 10/2020 | White et al. |
| 2020/0402648 A1* | 12/2020 | Ghosh .............. G16H 20/10 |
| 2020/0410601 A1 | 12/2020 | Laumeyer et al. |
| 2021/0012904 A1 | 1/2021 | Simon et al. |
| 2021/0045682 A1 | 2/2021 | Poon et al. |
| 2021/0142914 A1 | 5/2021 | Hua et al. |
| 2021/0151180 A1 | 5/2021 | Sudharsan |
| 2024/0047032 A1 | 2/2024 | Hansen et al. |

FOREIGN PATENT DOCUMENTS

| | | |
|---|---|---|
| WO | 2016/138102 A1 | 9/2016 |
| WO | 2021/076652 A1 | 4/2021 |

OTHER PUBLICATIONS

Final Office Action for U.S. Appl. No. 16/689,314, dated Nov. 23, 2022, (67 pages), United States Patent and Trademark Office, US.

Final Rejection Mailed on Sep. 6, 2023 for U.S. Appl. No. 16/689,288, 17 page(s).

Advisory Action for U.S. Appl. No. 16/689,289, dated May 11, 2023, (3 pages), United States Patent and Trademark Office, US.

NonFinal Office Action for U.S. Appl. No. 16/689,314, dated Jul. 27, 2023, (36 pages), United States Patent and Trademark Office, US.

"Centricity Payer Connect," YouTube Video, GE Healthcare, (35 pages), Jun. 14, 2018. [Retrieved from the Internet Feb. 12, 2020]<https://www.youtube.com/watch?v=YD9RiCRjVu8&feature=youtu.be>.

"Payer-Provider Integration," YouTube Video, emids, Sep. 2, 2015, (7 pages). [Retrieved from the Internet Feb. 12, 2020] <https://www.youtube.com/watch?v=z_ByQh8-tUY>.

"Point of Care Assist, Powered by RxRevu," Cerner, (6 pages), (article, online), [Retrieved from the Internet Sep. 22, 2021] <URL: https://code.cerner.com/apps/rxrevu>.

"Premera—Prior Authorization," (25 pages), (article, online), https://www.premera.com/documents/036791.pdf.

Advisory Action for U.S. Appl. No. 16/689,288, dated Oct. 20, 2021, (4 pages), United States Patent and Trademark Office, USA.

Final Office Action for U.S. Appl. No. 16/689,288, dated Sep. 8, 2021, (18 pages), United States Patent and Trademark Office, USA.

Final Office Action for U.S. Appl. No. 16/689,289, dated Mar. 29, 2022, (44 pages), United States Patent and Trademark Office, USA.

Final Office Action for U.S. Appl. No. 16/689,314, dated Nov. 22, 2021, (73 pages), United States Patent and Trademark Office, USA.

Gu, Yingqi et al. "Predicting Medication Adherence Using Ensemble Learning and Deep Learning Models With Large Scale Healthcare Data," Scientific Reports, vol. 11, No. 18961, Sep. 23, 2021, pp. 1-13, available online: https://www.nature.com/articles/s41598-021-98387-w.

International Searching Authority, International Search Report and Written Opinion, Jun. 24, 2020, (19 pages), European Patent Office, Rijswijk, Netherlands.

International Searching Authority, Invitation to Pay Additional Fees and Partial Search Report for International Application No. PCT/US2019/062459, Feb. 19, 2020, (18 pages), European Patent Office, Rijswijk, The Netherlands.

NonFinal Office Action for U.S. Appl. No. 16/689,288, dated Feb. 18, 2022, (25 pages), United States Patent and Trademark Office, USA.

NonFinal Office Action for U.S. Appl. No. 16/689,288, dated Jul. 23, 2021, (33 pages), United States Patent and Trademark Office, USA.

NonFinal Office Action for U.S. Appl. No. 16/689,289, dated Sep. 24, 2021, (45 pages), United States Patent and Trademark Office, USA.

NonFinal Office Action for U.S. Appl. No. 16/689,314, dated May 10, 2021, (48 pages), United States Patent and Trademark Office, USA.

(56) References Cited

OTHER PUBLICATIONS

NonFinal Office Action for U.S. Appl. No. 16/689,314, dated May 16, 2022, (68 pages), United States Patent and Trademark Office, US.

Saiyed, Salim M. et al. "Differences, Opportunities, and Strategies in Drug Alert Optimization—Experiences of Two Different Integrated Health Care Systems," Applied Clinical Informatics, vol. 10, No. 5, pp. 777-782, DOI: 10.1055/s-0039-1697596.

Zahabi, Maryam et al. "Usability and Safety in Electronic Medical Records Interface Design: A Review of Recent Literature and Guideline Formulation," Human Factors The Journal of the Human Factors and Ergonomics, vol. 57, Issue 5, pp. 805-834, Published online: Mar. 23, 2015, Issue published: Aug. 1, 2015, DOI: 10.1177/0018720815576827.

"Fair Health Consumer," (5 pages), available online: www.fairhealthconsumer.org, accessed via web.archive.org for Dec. 23, 2017 (Year: 2017).

Notice of Allowance and Fees Due for U.S. Appl. No. 16/689,289, dated Jul. 21, 2023, (10 pages), United States Patent and Trademark Office, US.

NonFinal Office Action for U.S. Appl. No. 16/689,289, dated Aug. 9, 2022, (36 pages), United States Patent and Trademark Office, US.

Final Office Action for U.S. Appl. No. 16/689,289, dated Mar. 13, 2023, (46 pages), United States Patent and Trademark Office, US.

NonFinal Office Action for U.S. Appl. No. 16/689,288, dated Mar. 3, 2023, (16 pages), United States Patent and Trademark Office, US.

Advisory Action for U.S. Appl. No. 16/689,288, dated Dec. 13, 2023, (3 pages), United States Patent and Trademark Office, US.

Final Rejection Mailed on Feb. 15, 2024 for U.S. Appl. No. 16/689,314, 44 page(s).

Non-Final Rejection Mailed on Feb. 2, 2024 for U.S. Appl. No. 16/689,288, 19 page(s).

\* cited by examiner

| Classification Rule No. | 701<br>Classification Rule | 702<br>Recommendation Message | 703<br>Recommendation Logic |
|---|---|---|---|
| 1 | EOY PDC /= null, 1x fill and meets new to therapy logic used for OMTM, exclude 2+ fills, PM_ADR ≥10 | Counsel on new medication | Discuss importance of taking new medication as prescribed and potential barriers. |
| 2 | Current PDC /= null, ADR 0-7, and past max refill due date | Patient needs urgent refill of medication | Patient is late to refill. If continued therapy is appropriate, patient must fill medication immediately to remain adherent. |
| 3 | If member is ≥30 days past max refill due date with ADR ≥0 and current PDC /= null | Patient past due with no recent fill | Patient late to refill. If continued therapy is appropriate, discuss importance of taking medication as prescribed and potential barriers. |
| 4 | ≥1 day past refill due date, EOY PDC <90%, current PDC /= null and at least 1 day late to refill for prior 2 fills using refill due date, not max refill, ADR ≥0 | Remind patient to refill medication | Late to refill prior 2 fills. Counsel patient on timely refills and taking medication as prescribed. Ensure prescribing instructions match Rx directions at pharmacy. |
| 5 | ≥1 day past refill due date and EOY PDC <90%, ADR ≥0 or PM_ADR ≥10 | Remind patient to refill medication | Patient late to refill. |
| 6 | Current PDC = 40-60% and ADR ≥0 and consistently 30-90 days late to refill medication for at least 2 prior fills | Update Rx instructions if needed | Late to refill prior 2 fills. Counsel patient on timely refills and taking medication as prescribed. Ensure prescribing instructions match Rx directions at the pharmacy. |
| 7 | EOY PDC /= null and most recent day supply is <70 days, ADR ≥0 or PM_ADR ≥10 | Consider 3-month supply | Consider switching patient to 90-day fill, if appropriate. |
| 8 | EOY PDC /= null and most recent day supply is =90 days, ADR ≥0 or PM_ADR ≥10 | Consider 3-month supply | Patient has 100-day benefit. Consider switching patient to 100-day fill, if appropriate. |
| 9 | EOY PDC /= null and most recent day supply is <70 days, ADR ≥0 or PM_ADR ≥10 | Consider 3-month supply | Patient has 100-day benefit. Consider switching patient to 100-day fill, if appropriate. |
| 10 | Red 1yr, 1x in current year, exclude 2+ fills, PM_ADR ≥10 | Patient non-adherent in prior year | If continued therapy is appropriate, discuss importance of taking medication as prescribed and potential barriers. |
| 11 | members who ended previous year PDC <80%, active in 2021 but no fills yet (Using for YoY flip) | Patient non-adherent in prior year | If continued therapy is appropriate, discuss importance of taking medication as prescribed and potential barriers. |

FIG. 7

MACHINE LEARNING TECHNIQUES FOR PROSPECTIVE EVENT-BASED CLASSIFICATION

CROSS-REFERENCES TO RELATED APPLICATIONS

The present application claims priority to U.S. Provisional Patent Application No. 63/261,496 (filed on Sep. 22, 2021), which is incorporated by reference herein in its entirety.

BACKGROUND

Various embodiments of the present invention address technical challenges related to performing predictive data analysis. Various embodiments of the present invention address the shortcomings of existing predictive data analysis systems and disclose various techniques for efficiently and reliably performing predictive data analysis.

BRIEF SUMMARY

In general, embodiments of the present invention provide methods, apparatus, systems, computing devices, computing entities, and/or the like for performing predictive data analysis. Certain embodiments of the present invention utilize systems, methods, and computer program products that perform predictive data analysis by using at least one of prospective coverage score determination machine learning models and prospective event-based classification machine learning models.

In accordance with one aspect, a method is provided. In one embodiment, the method comprises: generating, based at least in part on the one or more predictive input events, a current coverage score for the observation period; executing a prospective coverage score determination machine learning model to generate, based at least in part on a plurality of prospective coverage model input features, a prospective coverage score for the predictive timeframe, wherein the plurality of prospective coverage model input features comprises one or more event distribution feature values associated with one or more predictive input events and one or more predictive entity feature values associated with the predictive entity; generating, based at least in part on a prospective coverage deviation measure for the prospective coverage score and a threshold coverage measure, a prospective coverage gap score for the predictive timeframe; determining, using a prospective event-based classification machine learning model, the prospective event-based classification, wherein: the prospective event-based classification machine learning model is configured to map the predictive entity to: identify a plurality of candidate prospective event-based classifications, and select the prospective event-based classification from the plurality of candidate prospective event-based classifications based at least in part on a group of classification input features comprising the current coverage score, the prospective coverage score, a current coverage gap score, and the prospective coverage score; and performing one or more prediction-based actions based at least in part on the prospective event-based classification.

In accordance with another aspect, a computer program product is provided. The computer program product may comprise at least one computer-readable storage medium having computer-readable program code portions stored therein, the computer-readable program code portions comprising executable portions configured to: generate, based at least in part on the one or more predictive input events, a current coverage score for the observation period; execute a prospective coverage score determination machine learning model to generate, based at least in part on a plurality of prospective coverage model input features, a prospective coverage score for the predictive timeframe, wherein the plurality of prospective coverage model input features comprises one or more event distribution feature values associated with one or more predictive input events and one or more predictive entity feature values associated with the predictive entity; generate, based at least in part on a prospective coverage deviation measure for the prospective coverage score and a threshold coverage measure, a prospective coverage gap score for the predictive timeframe; determine, using a prospective event-based classification machine learning model, the prospective event-based classification, wherein: the prospective event-based classification machine learning model is configured to map the predictive entity to: identify a plurality of candidate prospective event-based classifications, and select the prospective event-based classification from the plurality of candidate prospective event-based classifications based at least in part on a group of classification input features comprising the current coverage score, the prospective coverage score, a current coverage gap score, and the prospective coverage score; and perform one or more prediction-based actions based at least in part on the prospective event-based classification.

In accordance with yet another aspect, an apparatus comprising at least one processor and at least one memory including computer program code is provided. In one embodiment, the at least one memory and the computer program code may be configured to, with the processor, cause the apparatus to: generate, based at least in part on the one or more predictive input events, a current coverage score for the observation period; execute a prospective coverage score determination machine learning model to generate, based at least in part on a plurality of prospective coverage model input features, a prospective coverage score for the predictive timeframe, wherein the plurality of prospective coverage model input features comprises one or more event distribution feature values associated with one or more predictive input events and one or more predictive entity feature values associated with the predictive entity; generate, based at least in part on a prospective coverage deviation measure for the prospective coverage score and a threshold coverage measure, a prospective coverage gap score for the predictive timeframe; determine, using a prospective event-based classification machine learning model, the prospective event-based classification, wherein: the prospective event-based classification machine learning model is configured to map the predictive entity to: identify a plurality of candidate prospective event-based classifications, and select the prospective event-based classification from the plurality of candidate prospective event-based classifications based at least in part on a group of classification input features comprising the current coverage score, the prospective coverage score, a current coverage gap score for the predictive timeframe, and the prospective coverage score; and perform one or more prediction-based actions based at least in part on the prospective event-based classification.

BRIEF DESCRIPTION OF THE DRAWINGS

Figure 1:
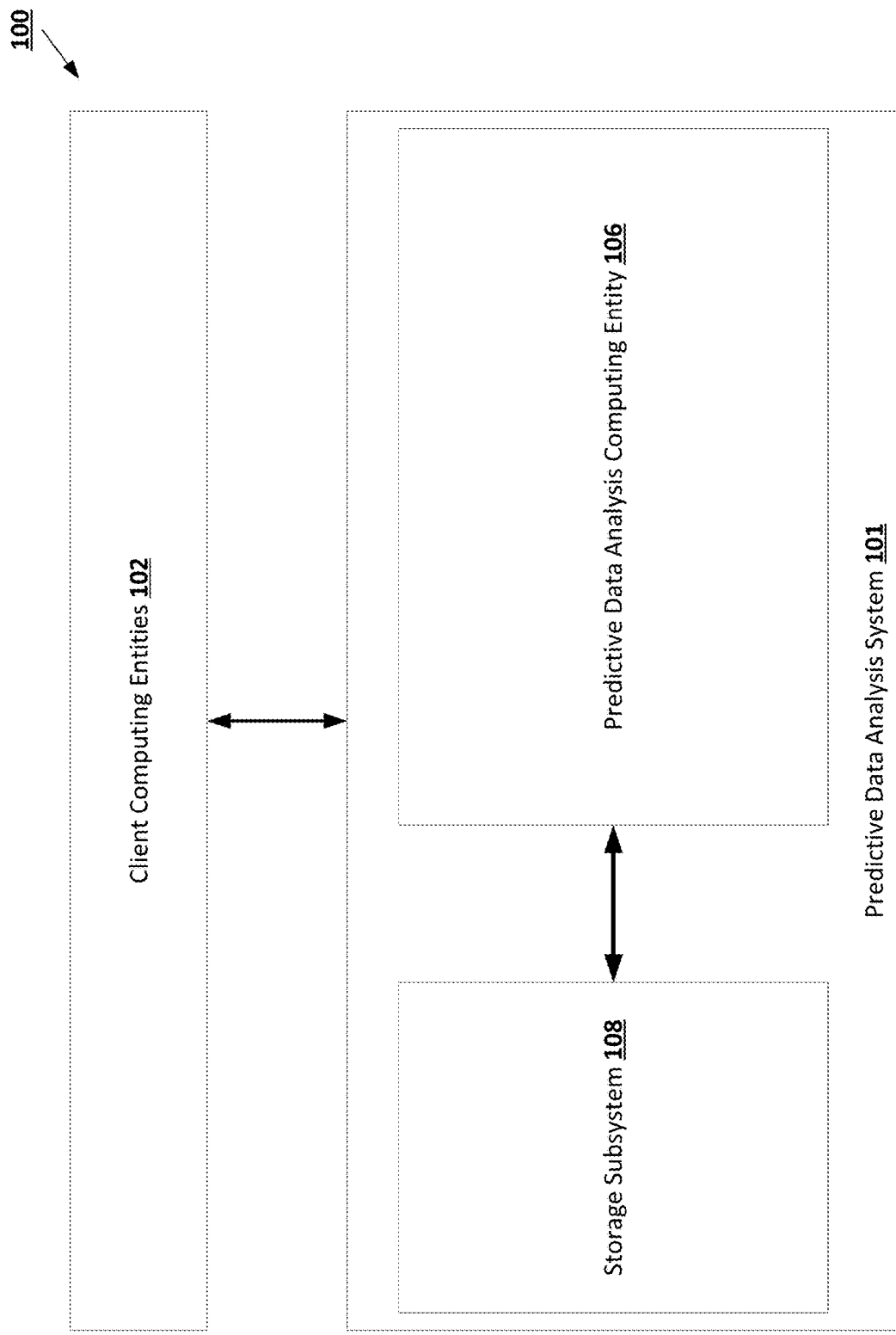

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
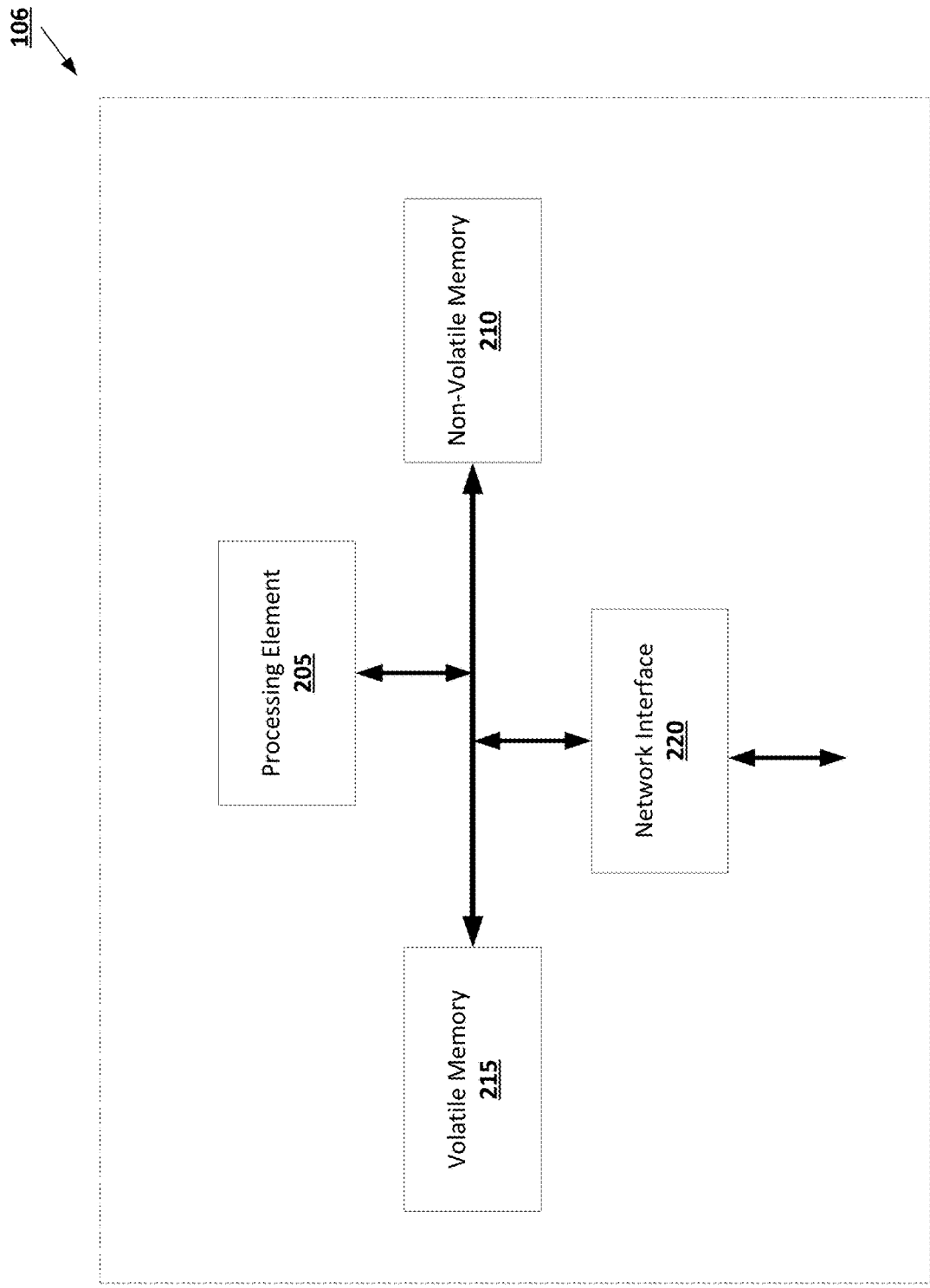

FIG. 2 provides an example predictive data analysis computing entity in accordance with some embodiments discussed herein.

Figure 3:
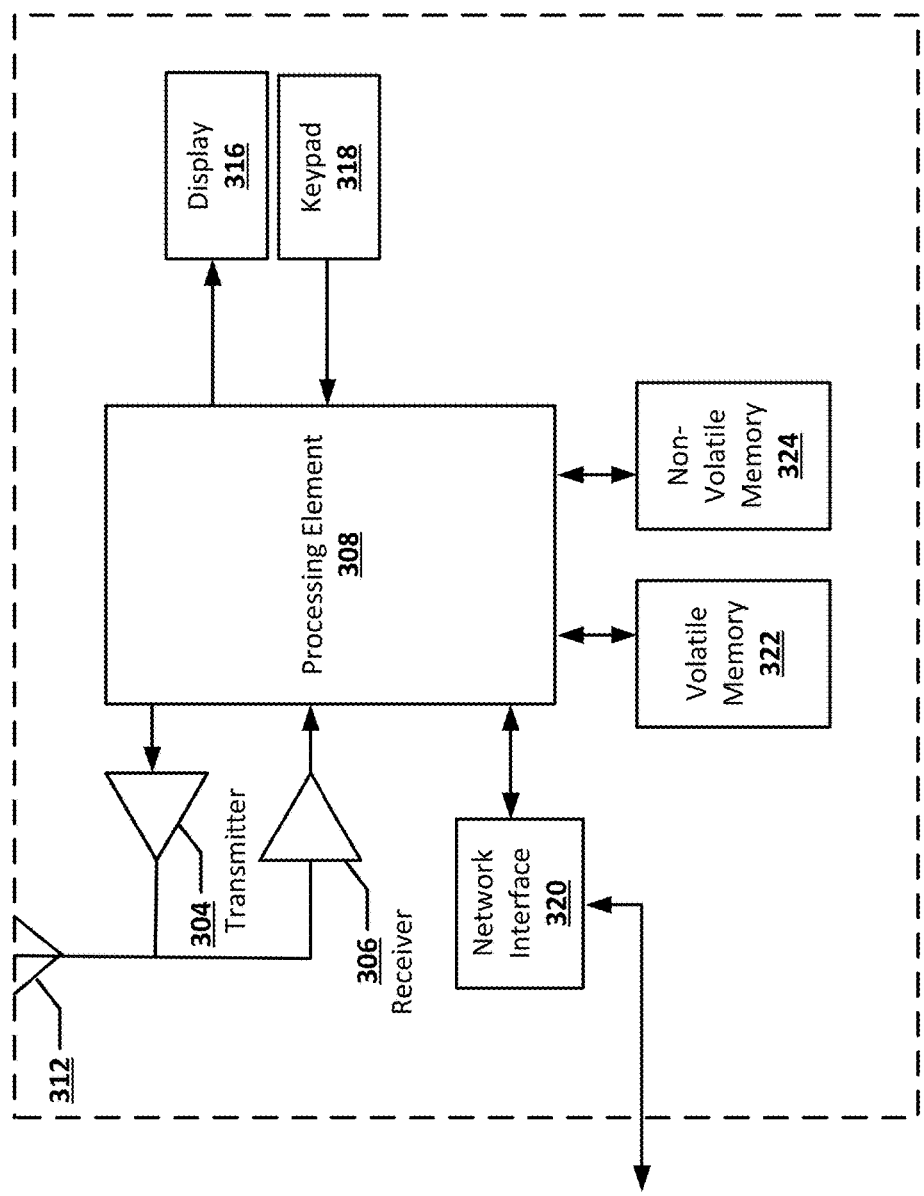

FIG. 3 provides an example external computing entity in accordance with some embodiments discussed herein.

Figure 4:
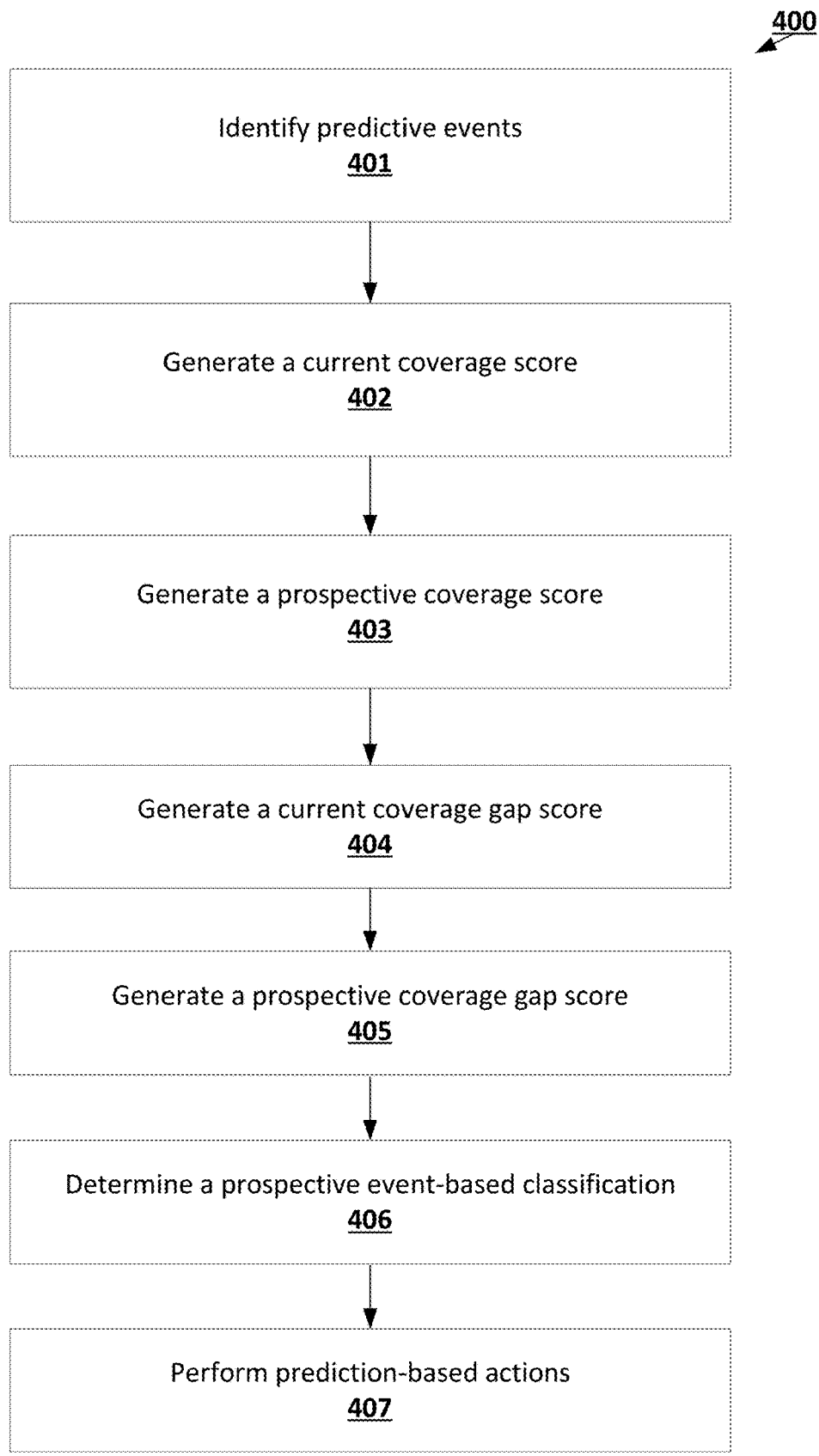

FIG. 4 is a flowchart diagram of an example process for determining a prospective event-based classification in accordance with some embodiments discussed herein.

Figure 5:
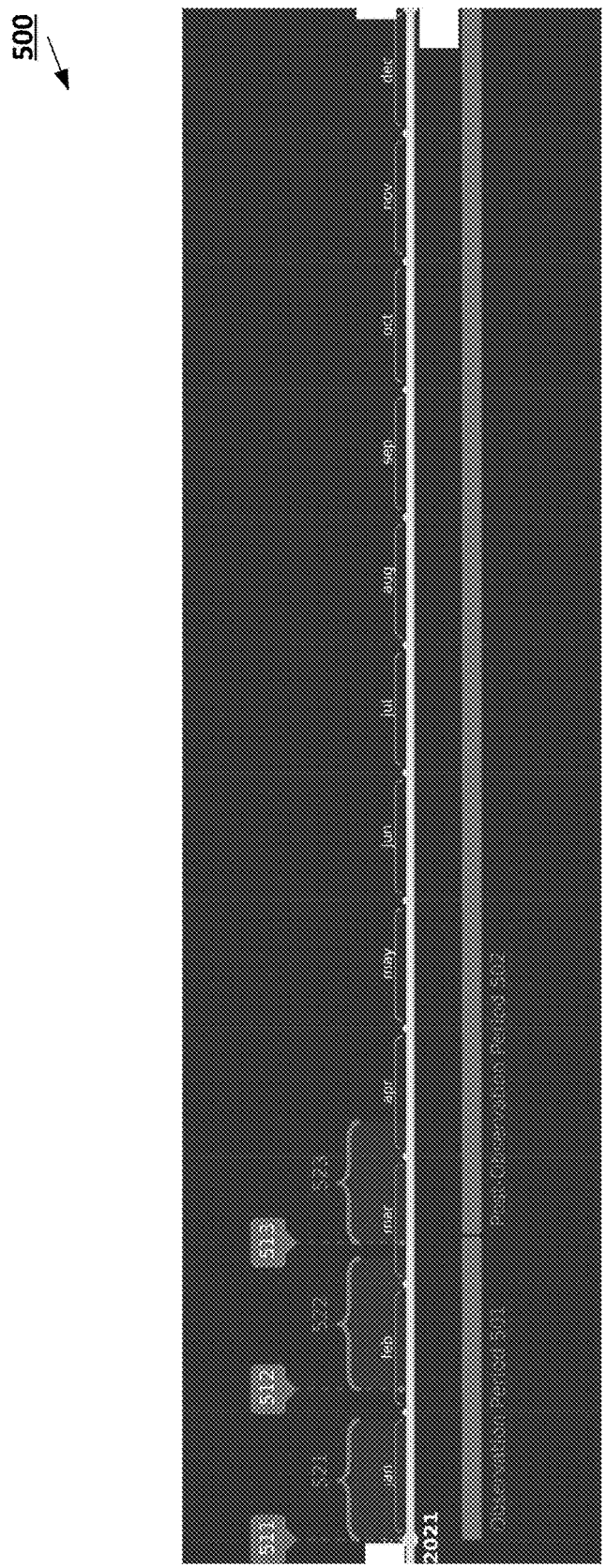

FIG. 5 provides an operational example of a predictive timeframe in accordance with some embodiments discussed herein.

Figure 6:
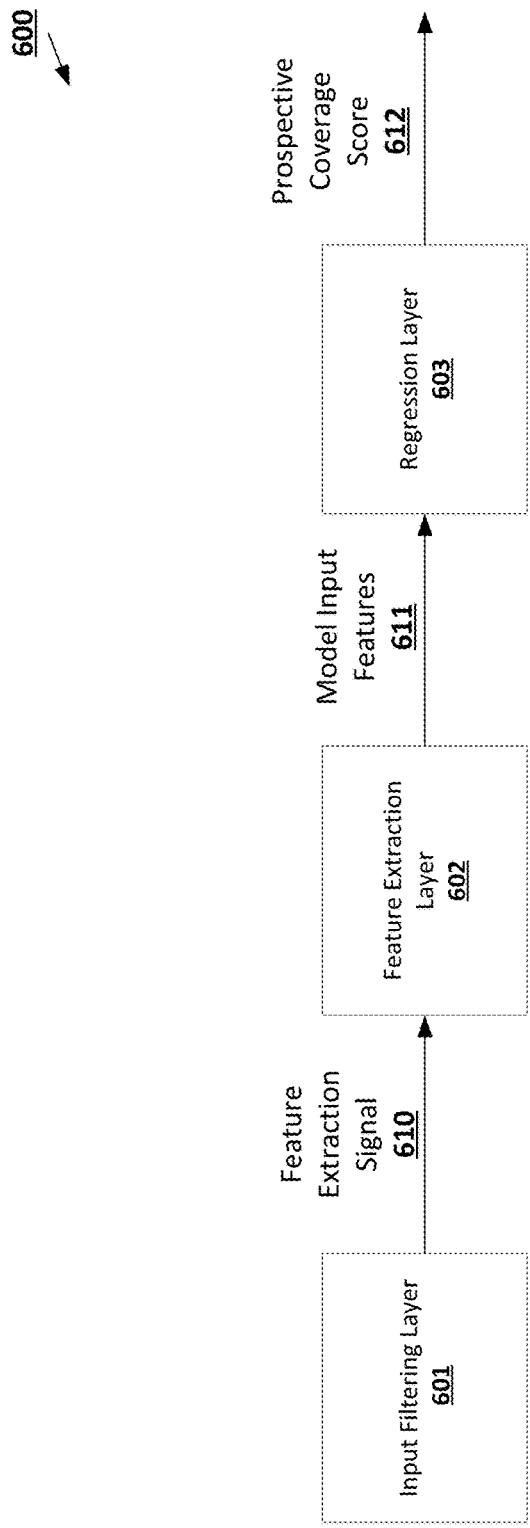

FIG. 6 provides an operational example of a prospective coverage score determination machine learning model in accordance with some embodiments discussed herein.

FIG. 7 provides an operational example of a recommendation message configuration data table in accordance with some embodiments discussed herein.

Figure 8:
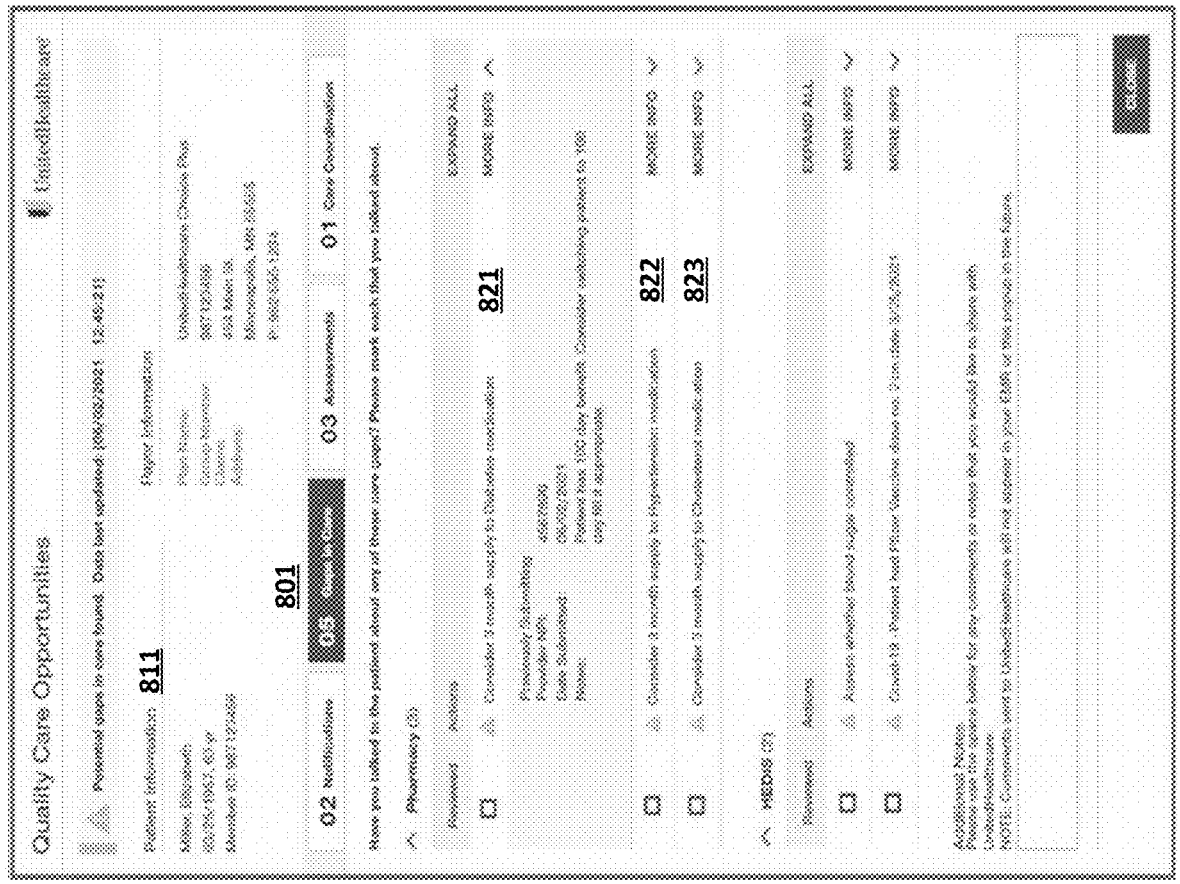

FIG. 8 provides an operational example of a prediction output user interface in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW AND TECHNICAL ADVANTAGES

Performing machine learning tasks such as classification using discrete timeseries-based forecasts is a substantial challenge facing the field of predictive data analysis. The obstacles involved are numerous: for example, given a predictive timeframe that includes an observation period and a post-observation period, it is not clear how to properly extract features describing observations of the observation period and features describing forecasts performed in relation to post-observation periods. As another example, because a discrete timeseries data object describes mere occurrence of events rather than continuous values associated with the events, it is not clear how to extract features in a way that takes into account relative significance of events as well as relative significance of temporal units (e.g., days) that are not associated with any event timestamps.

As a result of the above-noted obstacles, existing predictive data analysis systems require training of very deep machine learning models trained using extensive amounts of training data before such trained deep learning machine learning models can make reliable/accurate predictions when it comes to classifying entities based at least in part on discrete timeseries forecasts. This in turn translates to substantial computational load both on computer systems performing operations of the noted deep machine learning models and computer systems training the noted deep machine learning models. Moreover, because such extensive amounts of training data are necessary to provide adequate levels of reliability/accuracy of the deep machine learning models, these machine learning models may be, in practice, generally unusable for making predictions regarding certain individuals/circumstances that are associated with minimal amounts of relevant training data.

To address the obstacles associated with performing machine learning tasks such as classification using discrete timeseries-based forecasts, various embodiments of the present invention utilize machine learning models that perform prospective event-based classification based on features extracted based only on the observation period of a predictive timeframe as well as features extrapolated from the observation period data based on an assumption that trends of the observation period continue in the post-observation period. The noted solutions thus introduce computationally efficient methods for performing simultaneous timeseries-based forecasts using discrete timeseries data and using the forecast data along with observation data to perform classification tasks. This construction may reduce the amount of training data needed for reliability executing deep machine-learning classification models without substantially changing the level of accuracy associated with the machine-learning classification mechanism. In some embodiments, only a prospective coverage score is forecasted using a machine learning model, and all other feature values are linearly derived based on observation data and/or based on computed forecast data. By using the above-noted techniques, various embodiments of the present invention address technical challenges associated with performing machine learning tasks such as classification using discrete timeseries-based forecasts and reduce computational/storage load on predictive data analysis systems that are configured to perform machine learning tasks such as classification using discrete timeseries-based forecasts.

An exemplary application of various embodiments of the present invention relates to generating the medication adherence scores for selecting particular custom messages to be displayed to providers, based on additional context specific to the patient. In some embodiments, graphical user interface elements may be integrated as widgets or other graphical user interface elements of an electronic medical record (EMR) system executing at least partially on a user computing entity of a care provider (or a care providing facility). Aesthetics of the graphical user interface elements may be dictated based at least in part on style-indicating data (e.g., style sheets or other formatting models relevant to the EMR system) stored on the user computing entity for the EMR system, while the substantive content of the graphical user interface elements is dictated by relevant models and/or other data provided via API-based communication protocols relevant to a management computing entity and provided to the provider's user computing entity for display within graphical user interfaces of the EMR system.

Substantive data for provision within various graphical user interfaces may be generated based at least in part on the output of a machine-learning based model. As just one example, a machine-learning based model may be provided to generate a medication adherence score (e.g., via a linear regression model) for a patient based at least in part on historical data within the patient's EMR. In various embodiments, the machine learning model may be trained using supervised machine-learning techniques, using training data reflecting assigned medication adherence scores for certain patients and reflecting historical data reflecting the patient's adherence to certain medications. As just one example, the training data may comprise data indicating when a patient's prescription is due for a refill, when the patient actually refilled the prescription, whether the prescription refill was permissive or mandatory, the duration of each prescription refill, the type of refill (in-person or mail-order), and/or the like. In various embodiments, the model may additionally intake data reflecting social determinants of health, such as distance to a closest pharmacy, accessibility to transportation, and/or the like.

In certain embodiments, data indicative of the patient's historical pharmacy prescriptions, requirements for taking the prescriptions, requirements for picking-up refills of the prescriptions, and data indicative of the times/dates that the patient actually picked-up refills on the prescriptions, may be utilized as input to the machine-learning model. Additional data, such as demographic data, patient identification data, claim history data, and/or the like may additionally be provided as input to the machine-learning model. The output of the machine learning model provides a medication adherence score indicating whether the patient has historically demonstrated high, medium, or low adherence to a prescribed medication regimen. The score may be provided on a numerical scale or a tiered scale (e.g., low-adherence, moderate-adherence, high-adherence). In certain embodiments, the machine-learning based model is configured to provide a higher weight to more recent data, which may be more reflective of the patient's current likelihood of adhering to a medication regimen. In various embodiments, the machine learning model may be configured to output a plurality of medication adherence scores, such as an "all-time" adherence score and a "recent" adherence score. The all-time adherence score may reflect the patient's all-time medication adherence, reflecting all available EMR data (or a lengthy history). The recent adherence score may reflect the patient's medication adherence over a recent time period, such as based on EMR data generated in the current year (January 1-present), EMR data generated in the previous 12 months, EMR data generated in the previous 2 years, or another recent time period.

The output of the machine-learning based model may be provided to a matching table. The output of the machine-learning based model may be provided together with additional data of the patient, such as additional EMR related data, to identify one or more messages to be displayed for the patient. The messages may be medication specific, and may vary depending on the determined adherence score for the patient. Accordingly, certain messages may be dependent on a plurality of factors being present concurrently. For example, to display certain messages, the patient's recent and all-time medication adherence score may be required to be below a threshold (or otherwise indicate that the patient has a low recent and low all-time history of medication adherence), and the patient should be more than 30 days late to pick up at least one prescription, as reflected within the patient's EMR data. Other criteria may be single-factor criteria, such as only requiring that a patient be more than 30 days late to pick up at least one prescription.

In certain embodiments, the messages may be hierarchical, such that only a higher ranked message may be displayed if a plurality of messages are applicable to a patient. For example, if the patient has a low adherence score and has a prescription that is 30 days late, a first message requiring satisfaction of both of those criteria is displayed, instead of a second message that may require satisfaction of only a single criteria (e.g., only that the patient is 30-days late to pick up a prescription).

In some embodiments, the messages may be hierarchical based on assigned hierarchy labels (e.g., integer values) that provide a hierarchical relationship between multiple messages, such that assignment of one message is conditioned upon assignment of another message. In some embodiments, each messaged is associated with a set of scores, and the set of scores associated with different messages may be different. For example, in some embodiments, scores could be deemed relevant to a plurality of messages in certain embodiments, although the hierarchical structure of the messaging is then utilized to filter the relevant messages such that only the message with the highest hierarchical ranking is selected for display.

In certain embodiments, certain messages may be displayed, even if a higher ranked message is also displayed. The mapping table may apply additional criteria for displaying any of these certain messages, even if other messages are also displayed. For example, messages suggesting that the care provider prescribe a longer-duration prescription (e.g., a 100-day prescription, where a 30-day prescription is currently in effect) may be presented. In certain embodiments, such messages may be based at least in part on patient-specific data, such as data reflecting the patient's medical care plan benefits, which may indicate whether or not the patient is eligible for longer duration prescriptions. In certain embodiments, the messages may be at least partially customizable to reflect the longest-possible duration prescription that the patient is eligible for. For example, the message may have an embedded variable that may be populated with data reflecting a longest-available duration within the patient-specific data reflecting the patient's benefits.

In certain embodiments, the patient-specific data is updated continuously or periodically for each patient. As just one example, the patient-specific data is updated daily, and a new medication adherence score(s) is calculated for each patient after the patient-specific data is updated. Accordingly, once the machine-learning model is executed as a part of identifying a relevant statement for display for the patient, the statement reflects a recently updated set of patient-specific data.

In certain embodiments, once an action statement/message is generated for a patient by the management computing entity, the action statement/message is provided to a user computing entity of the provider to be integrated into a displayed widget within the EMR system executing at least in part on the user computing entity. In some embodiments, messages are provided to various EMR systems each having a different formatting system. In some embodiments, to enable messages to show up in a locally executed EMR system, an applet/program is installed at the EMR system (e.g., local at the provider's computer) that can translate the data received from our system and to provide appropriate formatting to generate the content of the widget. In some embodiments, the proposed server system determines all the appropriate formatting requirements for the widget, such that the data provided to the EMR system is executable to generate the widget inside the EMR system.

The content of a graphical user interface element, while dictated by relevant models and configurations of the management computing entity, are selected for display based on EMR data provided via the API-based communication protocol at the provider location. For example, data within a patient's EMR may be utilized to identify content for the management computing entity-based graphical user interface element. As a specific example, data within the patient's EMR indicative of hospital admissions and discharges, vaccine administration, historical medical treatment, and/or the like, may be utilized to populate at least a portion of a graphical user interface element after processing by the management computing entity. As just one example, a portion of the EMR data may be provided as input to a model for detecting suspected conditions of the patient, and the management computing entity may then generate an output indicating that a care provider should examine the patient to determine whether the suspect condition is relevant.

Analysis of data received from the EMR system by the management computing entity may comprise intake and tagging of the data (e.g., adding metadata tags to various data entries). Upon presentation within a generated graphical user interface, the metadata tags may be utilized to select a particular portion of the graphical user interface (e.g., within a tabbed region) of the graphical user interface.

In certain embodiments, the management computing entity executes a rule-based engine for reviewing data within each data record received and for assigning an appropriate metadata tag based at least in part on the content of the data record.

At least one graphical user interface may comprise a plurality of alternatively-accessible tabbed display regions, such as a "notifications" portion, a "gaps in care" portion, an "assessments" portion, and a "care coordination" portion.

The notifications portion may be populated with data records having metadata tags of "admit," "discharge," or "vaccine." The displayed data may be further divided into subsections, such as "admits/discharges" and "vaccines."

The "gap in care" portion may be populated with data records having metadata tags of "pharmacy" or "HEDIS." Additional data records having metadata tags of "social determinants of health" may be included within the "gap in care" portion of the display. Moreover, the data displayed may be subdivided into relevant subsections within the display, such as "pharmacy" data and "HEDIS" data, as shown in the attached documentation. The content and/or format of each data record may be determined based at least in part on the type of data record as well as the content of the data record. Moreover, in certain embodiments, the content to be displayed within a data record may be determined based at least in part on external data, such as data stored within a payer-specific database that is identified and retrieved based at least in part on data provided to the management computing entity relevant to the particular data record. As shown, the data may comprise data indicating how a particular patient's healthcare plan impacts the pharmaceutical prescriptions available to the patient. Moreover, gaps in care may be determined based at least in part on expected care procedures that may be identified by the management computing entity and upon determining that one or more medical treatments expected within the expected care procedures are not reflected within the EMR data. One or more models (e.g., rule-based models or machine-learning based models) executed by the management computing entity are utilized to identify gaps in care as well as the content of data records displayed via the graphical user interface element displayed within the EMR system graphical user interface.

Within the "assessments" tab portion of the graphical user interface element, the management computing entity may populate data indicating one or more suspected medical conditions that may be relevant to the patient based at least in part on content within the patient's EMR. In certain embodiments, a determination that a patient's EMR is indicative of one or more suspect conditions may be made based at least in part on output of a model (e.g., a machine learning model) for identifying suspected conditions that may be relevant to a particular patient based at least in part on the patient's EMR.

Within the "care coordination" tab, content may be populated exclusively from the management computing entity, such as data generated based at least in part on a patient's healthcare plan, which may be data accessible to the management computing entity. The content of the "care coordination" tabbed graphical user interface element comprises data suggesting various care coordination aspects that may be relevant to the patient, based at least in part on the patient's healthcare coverage. These data records may help a provider to plan a visit for a patient by providing a list of talking points/action items to complete during the visit. In light of the various data content types to be provided via the discussed graphical user interface elements, the management computing system operates as a data aggregator and a data disseminator, for receiving data from the EMR system (e.g., via an API-based communication protocol), for providing data as input to one or more models, for receiving data as output from one or more models, and for providing data for display within the graphical user interface element via an API-based communication protocol to a provider's user computing entity for display within the graphical user interface of the EMR system. In various embodiments, data displayed via one or more of the tabbed graphical user interface elements may be interactive, and may be utilized for initializing one or more additional processes relevant to the data.

II. DEFINITIONS

The term "predictive entity" may refer to a data construct that describes a real-world entity and/or a virtual entity with respect to which one or more predictive data analysis tasks are performed. An example of a predictive entity is a predictive entity that corresponds to a member/patient profile. In some embodiments, data associated with the predictive entity (e.g., event data associated with the predictive entity) are used to generate a prospective event-based classification for the predictive entity with respect to a predictive timeframe.

The term "event category" may refer to a data construct that describes a grouping (e.g., a subject-matter-based grouping) of predictive input events associated with a predictive entity. For example, in some embodiments, when a predictive entity is associated with d medications/prescriptions, then the prescription fill events associated with each of the d medications/prescriptions are grouped into an event grouping that is associated with an event category corresponding to the particular medication/prescription.

The term "predictive input event" may refer to a data construct that describes features associated with an observed/recorded event, where the event has occurred in relation to a predictive entity and an event category. An example of a predictive input event is an observed/recorded prescription fill event that describes that a particular medication (that is associated with the event category) is filled at a particular fill time/date (i.e., a particular event time) for a particular patient/member (that is associated with the predictive entity). In some embodiments, in addition to an associated predictive entity (e.g., a particular patient/member), an associated event time (e.g., a particular fill time/ date), and an associated event category (e.g., a particular medication) a predictive input event is associated with an expected cross-event temporal gap measure. The expected cross-event temporal gap measure for an predictive input event may describe an expected measure of temporal gap (e.g., an expected number of days) between the predictive input event and a successive predictive input event for the predictive entity in relation to the event category. For example, when the predictive input event describes an observed/recorded prescription fill event for a particular patient/member and a particular prescription, then the expected cross-event temporal gap measure for the predictive input event may describe a next allowed refill date of the particular prescription (e.g., if the next allowed refill date is 30 days after the event time of the predictive input event, then the expected cross-event temporal gap measure for the predictive input event may be 30.

The term "predictive timeframe" may refer to a data construct that describes a defined period of time with respect to which a prospective event-based classification is generated. An example of a predictive timeframe is a calendar year timeframe. In some embodiments, a predictive timeframe includes an observation period and a post-observation period, where the prospective event-based classification for the predictive timeframe is generated based at least in part on predictive input events associated with the observation period only. A predictive timeframe may describe a defined time period, where events associated with the predictive entity that occur within the defined time period are used to determine a classification for the predictive entity. For example, the classification may be a medication adherence classification for a patient/member that is associated with the predictive entity during a predictive timeframe of one year, such as a predictive timeframe that starts with Jan. 1, 2021 and ends with Dec. 31, 2021. In this example, the prescription fill events of the patient/member within the predictive timeframe may be used to determine the medication adherence classification. Importantly, the predictive timeframe includes an observation period (e.g., a past to present period) associated with the n observed/recorded predictive input events and a post-observation period (e.g., a future period) that is not associated with any of the n observed/recorded predictive input events. In other words, all of the n observed/recorded predictive input events having event times that fall within the observation period, while the observation period is only a part of the total predictive timeframe that includes a post-observation period for which no observed/recorded predictive input events are available and/or no observed/recorded predictive input events are used to determine the classification. Accordingly, the classification generated for a predictive entity in relation to an event category and a predictive timeframe may be a prospective event-based classification: event-based because the classification is determined based at least in part on predictive input events that occur within the predictive timeframe and in relation to the predictive entity and the event category, and prospective because the classification is determined based at least in part on predictive input events associated with only a portion of the predictive timeframe (i.e., the observation period of the predictive timeframe, while excluding the post-observation period of the predictive timeframe).

The term "current coverage score" may refer to a data construct that describes a value that, when having a non-null value, describes an observed ratio (i.e., a computed ratio) of an observed coverage count for n predictive input events of an observation period to an observation period count of the observation period. An example of a current coverage score is a current coverage score that is determined based at least in part on a Proportion of Days (PDC) score for an observation period having n predictive input events. In some embodiments, the current coverage score for an observation period either has a null value or a non-null value. A null current coverage score may be determined when either of the following two conditions are satisfied: (i) a dual-event entity categorization indicator for a predictive entity that is associated with the observation period is a negative dual-event entity categorization indicator, or (ii) an observation exclusion indicator for a predictive entity that is associated with the observation period is an affirmative observation exclusion indicator. A non-null current coverage score may be determined when both of the following two conditions are satisfied: (i) a dual-event entity categorization indicator for a predictive entity that is associated with the observation period is an affirmative dual-event entity categorization indicator, and (ii) an observation exclusion indicator for a predictive entity that is associated with the observation period is a negative observation exclusion indicator. In some embodiments, the non-null current coverage score for an observation period is determined based at least in part on a PDC score for the observation period.

The term "dual-event entity categorization indicator" may refer to a data construct that describes whether an event count for a particular observation period for a particular predictive entity satisfies a current computation threshold (e.g., exceeds a current computation threshold value, such as a current computation threshold value of one). In some embodiments, when the event count for a particular observation period (i.e., the number of predictive input events in the particular observation period) satisfies the current computation threshold, the dual-event entity categorization indicator for the observation period is an affirmative dual-event entity categorization indicator. In some embodiments, when the event count for a particular observation period fails to satisfy the current computation threshold, then the dual-event entity categorization indicator for the observation event is a negative dual-event entity categorization indicator. For example, given system configuration data defining that the dual-event entity categorization indicator for a given observation period is an affirmative dual-event entity categorization indicator if the event count for the given observation period exceeds one (i.e., is two or more), then given an observation period having an event count of three (e.g., the observation period 501 that is associated with three predictive input events 511-513), then the dual-event entity categorization indicator for the noted observation period may be an affirmative dual-event entity categorization indicator. As another example, given system configuration data defining that the dual-event entity categorization indicator for a given observation period is an affirmative dual-event entity categorization indicator if the event count for the given observation period exceeds one (i.e., is two or more), then given an observation period having an event count of one (e.g., having only one predictive input events in the observation period), then the dual-event entity categorization indicator for the noted observation period may be a negative dual-event entity categorization indicator. In some embodiments, the current computation threshold value is set to one, as Center for Medicare Services (CMS) guidelines requires at least two prescription fill events before calculating a PDC score for a member/patient.

The term "observation exclusion indicator" may refer to a data construct that describes a predictive entity that satisfies at least one observation exclusion condition. In some embodiments, if the predictive entity satisfies at least one observation exclusion condition, the observation exclusion indicator for the predictive entity is an affirmative observation exclusion indicator. In some embodiments, if the predictive entity does not satisfy any observation exclusion conditions, the observation exclusion indicator for the predictive entity is a negative observation exclusion indicator. Operational examples of observation exclusion conditions include conditions defined by CMS for medication adherence (e.g., PDC) observation.

The term "observed coverage count" may refer to a data construct that describes a computed number of temporal units (e.g., days) within an observation period that are covered by the n predictive input events of the observation period. In some embodiments, the observed coverage count is determined using the following operation: (i) for each of the n predictive input events of the observation period, determining a per-event coverage period that starts with the event time for the predictive input event and goes on for a number of successive temporal units that fall within a post-event period after the predictive input event whose duration is determined based at least in part on the expected cross-event temporal gap measure for the predictive input event, and (ii) computing the observed coverage count based at least in part on the number of temporal units within the observation period that fall within one of the n per-event coverage periods for the n predictive input events. For example, if a predictive input event occurs on Jan. 1, 2021, and if the expected cross-event temporal gap measure for the predictive input event is 30, then the per-event coverage period for the predictive input event runs from Jan. 1, 2021 to Jan. 30, 2021.

The term "prospective coverage score" may refer to a data construct that describes a value that, when having a non-null value, describes a prediction about what the current coverage score for an observation period that includes the entirety of a predictive timeframe will be at the end of the predictive timeframe. A null prospective coverage score may be determined when either of the following two conditions are satisfied: (i) a single-event entity categorization indicator for a predictive entity that is associated with the observation period is a negative single-event entity categorization indicator, or (ii) an observation exclusion indicator for a predictive entity that is associated with the observation period is an affirmative observation exclusion indicator. A non-null prospective score may be determined when both of the following two conditions are satisfied: (i) a single-event entity categorization indicator for a predictive entity that is associated with the observation period is an affirmative single-event entity categorization indicator, and (ii) an observation exclusion indicator for a predictive entity that is associated with the observation period is a negative observation exclusion indicator. In some embodiments, the non-null prospective coverage score for a predictive timeframe is determined based at least in part on a predicted PDC score for the predictive timeframe. In some embodiments, the prospective coverage score for a predictive timeframe is determined based at least in part on the output of a prospective coverage score determination machine learning model that is configured to comprise prospective coverage model input features associated with the predictive timeframe to generate a prospective coverage score for the predictive timeframe.

The term "single-event entity categorization indicator" may refer to a data entity that describes whether an event count for a particular observation period for a particular predictive entity satisfies a prospective computation threshold (e.g., exceeds a prospective computation threshold value, such as a prospective computation threshold value of zero). In some embodiments, when the event count for a particular observation period satisfies the current computation threshold, then the single-event entity categorization indicator for the observation period is an affirmative single-event entity categorization indicator. In some embodiments, when the event count for a particular observation period fails to satisfy the current computation threshold, the single-event entity categorization indicator is a negative single-event entity categorization indicator. For example, given system configuration data defining that the single-event entity categorization indicator for a given observation period is an affirmative single-event entity categorization indicator if the event count for the given observation period exceeds zero (i.e., is one or more), then given an observation period having an event count of three (e.g., the observation period 501 that is associated with three predictive input events 511-513), then the single-event entity categorization indicator for the noted observation period may be an affirmative single-event entity categorization indicator. As another example, given system configuration data defining that the single-event entity categorization indicator for a given observation period is an affirmative single-event entity categorization indicator if the event count for the given observation period exceeds zero (i.e., is zero or more), then given an observation period having an event count of one (e.g., having only one predictive input events in the observation period), then the single-event entity categorization indicator for the noted observation period may be a negative single-event entity categorization indicator. In some embodiments, the current computation threshold value is set to zero, such that at least one prescription fill event should be recorded/observed before calculating a predicted end-of-year PDC score for a member/patient.

The term "prospective coverage score determination machine learning model" may refer to a data construct having executable aspects and that describes parameters, hyper-parameters, and/or defined operations of a machine learning model, where the machine learning model is configured to process a group of prospective coverage model input features for a predictive timeframe (e.g., comprising a plurality of event distribution feature values associated with an observation period of the predictive timeframe and one or more predictive entity feature values associated with a corresponding predictive entity) to determine a prospective coverage score for the predictive timeframe. The prospective coverage score determination machine learning model may be trained based at least in part on historical data describing historically observed coverage scores for one or more historical timeframes having time durations that are equivalent to a time duration of the predictive timeframe. For example, the training data used to train the prospective coverage score determination machine learning model may include a set of training entries, where each training entry describes a computed/observed current coverage score for a particular historical predictive timeframe at the end of the particular historical predictive timeframe. In some embodiments, the prospective coverage score determination machine learning model is generated by changing the parameters of the prospective coverage score determination machine learning model to optimize an error function that is determined based at least in part on inferred prospective coverage scores for the historical predictive timeframes and the computed/observed current coverage scores for the historical predictive timeframes. In some embodiments, inputs to a prospective coverage score determination machine learning model include a vector describing prospective coverage model input features of an input predictive timeframe, while the outputs of the prospective coverage score determination machine learning model include an atomic value describing a prospective coverage score for the input predictive timeframe.

The term "event distribution feature value" may refer to a data construct that describes a property of a predictive timeframe that is determined based at least in part on an assumed occurrence of predictive input events during the post-observation period of the predictive timeframe. As noted above, the predictive timeframe may include an observation period that is associated with a set of observed/recorded predictive input events and a post-observation period that is not associated with any observed/recorded predictive input events. In some embodiments, an event distribution feature value describes a property of the predictive timeframe that is determined based at least in part on the set of observed/recorded predictive input events associated with the observation period of the predictive timeframe and an assumed set of predictive input events during the post-observation period of the predictive timeframe. For example, a particular event distribution feature value (referred to herein as a minimal prospective coverage score) may describe an expected current coverage score of the predictive timeframe that is determined at the end of the predictive timeframe, where the expected current coverage score is determined based at least in part on the set of observed/recorded predictive input events associated with the observation period of the predictive timeframe and an assumed empty set of predictive input events during the post-observation period of the predictive timeframe. As another example, a particular event distribution feature value (referred to herein as a maximal prospective coverage score) may describe an expected current coverage score of the predictive timeframe that is determined at the end of the predictive timeframe, where the expected current coverage score is determined based at least in part on the set of observed/recorded predictive input events associated with the observation period of the predictive timeframe and an assumed set of predictive input events during the post-observation period of the predictive timeframe that ensure that all of the temporal units of the post-observation period of the predictive timeframe are covered by an assumed predictive input event.

The term "minimal coverage score" may refer to a data construct that describes an event distribution feature value that describes a predicted minimal coverage score for the predictive timeframe assuming minimal event coverage during a post-observation period of the predictive timeframe. In other words, the minimal coverage score may describe an expected current coverage score for the predictive timeframe that is determined by assuming that none of the temporal units in the post-observation period of the predictive timeframe is covered by any predictive input events. In some embodiments, given a predictive timeframe that includes $d_1$ temporal units in the observation period and $d_2$ in the post-observation period, where the $d_3$ days of the observation period are covered by recorded/observed predictive input events, the minimal coverage score for the predictive timeframe is determined based at least in part on (e.g., based at least in part on a computed ratio of) a minimal coverage count that is determined based at least in part on $d_3+0$ and an observation period count that is determined based at least in part on $d_1+d_2$.

The term "maximal event coverage score" may refer to a data construct that describes an event distribution feature value that describes a predicted maximal coverage score for the predictive timeframe assuming maximal event coverage during a post-observation period of the predictive timeframe. In other words, the maximal coverage score may describe an expected current coverage score for the predictive timeframe that is determined by assuming that all of the temporal units in the post-observation period of the predictive timeframe are covered by predictive input events. In some embodiments, given a predictive timeframe that includes $d_1$ temporal units in the observation period and $d_2$ in the post-observation period, where the $d_3$ days of the observation period are covered by recorded/observed predictive input events, the maximal coverage score for the predictive timeframe is determined based at least in part on (e.g., based at least in part on a computed ratio of) a minimal coverage count that is determined based at least in part on $d_3+d_2$ and an observation period count that is determined based at least in part on $d_1+d_2$.

The term "current coverage gap score" may refer to a data construct that describes a value that, when having a non-null value, a measure of deviation between a current coverage score for a predictive timeframe and a threshold coverage score. An example of a threshold coverage score is an 0.80 threshold coverage score (e.g., a threshold PDC measure of 80% as defined by CMS). For example, in some embodiments, a non-null current coverage describes a maximum number of temporal units (e.g., days) within a post-observation period of the predictive timeframe that can be uncovered by any predictive input events (e.g., prescription fill events) before the current coverage score for the predictive timeframe falls below the threshold coverage score. Accordingly, in some embodiments, a non-null current coverage score describes a largest discrete value for a computed number of uncovered temporal units in the post-observation period of the predictive timeframe that can nevertheless lead to a positive current coverage deviation measure for the current coverage score and a threshold coverage score. Because of the negative relationship between the number of uncovered temporal units in a period and the current coverage score of that period, at some point an increasing number of uncovered temporal units will cause the current coverage score to go below the threshold coverage score. In some embodiments, the current coverage gap score describes the discrete value for the number of uncovered temporal units in the period that will cause the measure of deviation between the current coverage score for the period and the threshold coverage score to attain its minimal non-negative value. Naturally, this measure depends on the value of the current coverage score, which in turn may depend on the number of temporal units in the period that are covered by predictive input events. In some embodiments, when the current coverage score has a null value, the current coverage gap score also has a null value.

The term "prospective coverage gap score" may refer to a data construct that describes a value that, when having a non-null value, a measure of deviation between a current prospective score for a predictive timeframe and a threshold coverage score. As described above, an example of a threshold coverage score is an 0.80 threshold coverage score (e.g., a threshold PDC measure of 80% as defined by CMS). For example, the prospective coverage gap score for a predictive timeframe may describe, assuming a particular prospective coverage score for the predictive timeframe that describes a predicted end-of-timeframe (e.g., year-end) current coverage score for the predictive timeframe, a measure of deviation between: (i) a first number of temporal units (e.g., days) in the predictive timeframe that are predicted to not be covered by any predictive input events under the assumption that the end-of-timeframe (e.g., year-end) current coverage score for the predictive timeframe indeed equals the particular prospective coverage score, and (ii) a second number of temporal units (e.g., days) in the predictive timeframe that, when covered by predictive input events, cause prospective coverage deviation measure to have its largest negative value. In some embodiments, the first number noted above is generated based at least in part on a*b, where a is the predictive coverage score for the predictive timeframe and b is the total number of days (i.e., the predictive timeframe count) of the predictive timeframe. In some embodiments, the second number noted above is the largest value of t such that (t/b)<0, where t is an assumed number of covered temporal units in the predictive timeframe and b is the total number of days (i.e., the predictive timeframe count) of the predictive timeframe. In some embodiments, when the prospective coverage score has a null value, the prospective coverage gap score also has a null value.

The term "prospective event-based event classification" may refer to a data construct that describes a predicted designation for a predictive entity (e.g., for a patient/member) in the totality of a predictive timeframe that is determined based at least in part on predictive input events observed/recorded during only a portion (i.e., an observation period) of the noted predictive timeframe. An example of a prospective event-based classification is a medication adherence classification for a patient/member during a year that is determined based at least in part on observed/recorded medication fill events of the patient/member during only a portion of the year. In some embodiments, the prospective event-based classification is event-based because the prospective event-based classification is determined based at least in part on predictive input events that occur within the predictive timeframe and in relation to the predictive entity and the event category. In some embodiments, the prospective event-based classification is prospective because the prospective event-based classification is determined based at least in part on predictive input events associated with only a portion of the predictive timeframe (i.e., the observation period of the predictive timeframe, while excluding the post-observation period of the predictive timeframe).

The term "prospective event-based classification machine learning model" may refer to a data construct having executable aspects and that describes parameters, hyper-parameters, and/or defined operations of a machine learning model (e.g., a rule-based machine learning model), where the machine learning model is configured to process a group of classification input features for a predictive entity to determine a prospective event-based classification for the predictive entity. In some embodiments, the prospective event-based classification machine learning model maps a predictive entity to a selected prospective event-based classification of a set of candidate prospective event-based classifications. To do so, the prospective event-based classification machine learning model may use one or more classification engines. For example, in some embodiments, the prospective event-based classification machine learning model may use m classification engines each having a learned/trained/predefined engine weight to generate m per-engine selected prospective event-based classifications for a predictive entity, then generate a classification score for each candidate prospective event-based classification based learned/trained/predefined engine weights of a subset of the m classification engine that have recommended the candidate prospective event-based classification as their respective per-engine selected prospective event-based classifications, and then select a candidate prospective event-based classification having a highest classification score as the prospective event-based classification for the predictive entity. As another example, the prospective event-based classification machine learning model may use m classification engines each having a learned/trained/predefined engine weight to generate m per-engine selected prospective event-based classifications for a predictive entity, then generate a classification score for each candidate prospective event-based classification based learned/trained/predefined engine weights of a subset of the m classification engine that have recommended the candidate prospective event-based classification as their respective per-engine selected prospective event-based classifications, and then select a subset of candidate prospective event-based classifications having a threshold-satisfying classification score as the prospective event-based classifications for the predictive entity. Examples of classification engines that can be used by a prospective event-based classification machine learning model include rule-based classification engines, feedforward neural network classification engines, clustering classification engines, and recurrent neural network engines. In some embodiments, a rule-based classification engine is configured to recommend a selected prospective event-based classification for a predictive entity based at least in part on whether a group of classification input features for the predictive entity satisfy one or more of a set of classification rules.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query, or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established, or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically configured machines performing the steps or operations specified in the block diagrams and flowchart illustrations. Accordingly, the block diagrams and flowchart illustrations support various combinations of embodiments for performing the specified instructions, operations, or steps.

IV. EXEMPLARY SYSTEM ARCHITECTURE

FIG. 1 is a schematic diagram of an example architecture 100 for performing health-related predictive data analysis. The architecture 100 includes a predictive data analysis system 101 configured to receive health-related predictive data analysis requests from external computing entities 102, process the predictive data analysis requests to generate predictions, provide the generated predictions to the external computing entities 102, and automatically perform prediction-based actions based at least in part on the predictions. Examples of prediction-based actions include generating and/or displaying medication-adherence-related messages to a provider and/or to a patient/member.

In some embodiments, predictive data analysis system 101 may communicate with at least one of the external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive predictive data analysis requests from one or more external computing entities 102, process the predictive data analysis requests to generate predictions corresponding to the predictive data analysis requests, provide the predictions to the external computing entities 102, and automatically perform prediction-based actions based at least in part on the generated predictions.

The storage subsystem 108 may be configured to store input data used by the predictive data analysis computing entity 106 to perform health-related predictive data analysis as well as model definition data used by the predictive data analysis computing entity 106 to perform various health-related predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include or be in communication with one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the predictive data analysis computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include or be in communication with one or more input elements, such as a keyboard input, a mouse input, a touch screen/display input, motion input, movement input, audio input, pointing device input, joystick input, keypad input, and/or the like. The predictive data analysis computing entity 106 may also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

As described below, to address the obstacles associated with performing machine learning tasks such as classification using discrete timeseries-based forecasts, various embodiments of the present invention utilize machine learning models that perform prospective event-based classification based on features extracted based only on the observation period of a predictive timeframe as well as features extracted by assuming trends of the observation period continue in the post-observation period. The noted solutions thus introduce computationally efficient methods for performing simultaneous timeseries-based forecasts using discrete timeseries data and using the forecast data along with observation data to perform classification tasks. In some embodiments, only a prospective coverage score is forecasted using a machine learning model, and all other feature values are linearly derived based on observation data and/or based on computed forecast data. By using the above-noted techniques, various embodiments discussed herein address technical challenges associated with performing machine learning tasks such as classification using discrete timeseries-based forecasts and reduce computational/storage load on predictive data analysis systems that are configured to perform machine learning tasks such as classification using discrete timeseries-based forecasts.

FIG. 4 is a flowchart diagram of an example process 400 for generating a prospective event-based classification for a predictive entity in relation to an event category. Via the various steps/operations of the process 400, the predictive data analysis computing entity 106 can use predictive input events associated with a portion of a predictive timeframe to determine a classification for the predictive entity in relation to the event category during the totality of the predictive timeframe. While various embodiments of the present invention describing selecting a single prospective event-based classification of a group of defined prospective event-based classifications for a predictive entity with respect to an event category and a predictive timeframe, a person of ordinary skill in the relevant technology will recognize that, in some embodiments, two or more prospective event-based classifications may be selected/assigned to a predictive entity with respect to an entity category and a predictive timeframe.

At step/operation 401, the predictive data analysis computing entity 106 identifies n predictive input events associated with the predictive entity, where the predictive input events are associated with the event category. An example of a predictive input event is an observed/recorded prescription fill event that describes that a particular medication (that is associated with the event category) is filled at a particular fill time/date (i.e., a particular event time) for a particular patient/member (that is associated with the predictive entity).

In some embodiments, in addition to an associated predictive entity (e.g., a particular patient/member), an associated event time (e.g., a particular fill time/date), and an associated event category (e.g., a particular medication) a predictive input event is associated with an expected cross-event temporal gap measure. The expected cross-event temporal gap measure for a predictive input event may describe an expected measure of temporal gap (e.g., an expected number of days) between the predictive input event and a successive predictive input event for the predictive entity in relation to the event category. For example, when the predictive input event describes an observed/recorded prescription fill event for a particular patient/member and a particular prescription, then the expected cross-event temporal gap measure for the predictive input event may describe a next allowed refill date of the particular prescription (e.g., if the next allowed refill date is 30 days after the event time of the predictive input event, then the expected cross-event temporal gap measure for the predictive input event may be 30).

In some embodiments, the n predictive input events are associated with an observation period of a predictive timeframe that includes the observation period and a post-observation period. A predictive timeframe may describe a defined time period, where events associated with the predictive entity that occur within the defined time period are used to determine a classification for the predictive entity. For example, the classification may be a medication adherence classification for a patient/member that is associated with the predictive entity during a predictive timeframe of one year, such as a predictive timeframe that starts with Jan. 1, 2021 and ends with Dec. 31, 2021. In this example, the prescription fill events of the patient/member within the predictive timeframe may be used to determine the medication adherence classification. Importantly, the predictive timeframe includes an observation period (e.g., a past to present period) associated with the n observed/recorded predictive input events and a post-observation period (e.g., a future period) that is not associated with any of the n observed/recorded predictive input events. In other words, all of the n observed/recorded predictive input events having event times that fall within the observation period, while the observation period is only a part of the total predictive timeframe that includes a post-observation period for which no observed/recorded predictive input events are available and/or no observed/recorded predictive input events are used to determine the classification.

Accordingly, the classification generated for a predictive entity in relation to an event category and a predictive timeframe may be an prospective event-based classification: event-based because the classification is determined based at least in part on predictive input events that occur within the predictive timeframe and in relation to the predictive entity and the event category, and prospective because the classification is determined based at least in part on predictive input events associated with only a portion of the predictive timeframe (i.e., the observation period of the predictive timeframe, while excluding the post-observation period of the predictive timeframe).

An operational example of a predictive timeframe 500 associated with the calendar year 2021 is depicted in FIG. 5. As depicted in FIG. 5, the predictive timeframe 500 includes an observation period 501 that begins on Jan. 1, 2021 and ends on Mar. 12, 2021, as well as a post-observation period 502 that begins on Mar. 13, 2021 and ends on Dec. 31, 2021. As further depicted in FIG. 5, the observation period 501 includes the following predictive input events: a first predictive input event 511 that is associated with an event time of Jan. 1, 2021, a second predictive input event 512 that is associated with an event time of Feb. 6, 2021, and a third predictive event 513 that is associated with an event time of Mar. 11, 2021.

In some embodiments, given the predictive timeframe 500 of FIG. 5, one objective of various embodiments of the present invention may be to determine a prospective event-based classification for all of the predictive timeframe 500 given the predictive input events 511-513. In some of the noted embodiments, the prospective event-based classification may be determined based at least in part on at least one of: (i) a current coverage score that may describe an observed ratio of an observed coverage count for the predictive input events 511-513 to an observation period count of the observation period 501, (ii) a prospective coverage score that may describe a predicted/forecasted current coverage score for the predictive timeframe 500 given the trends established by the predictive input events 511-513 and other feature data associated with the predictive entity, the event category, and/or the like, (iii) a deviation of the current coverage score and a threshold coverage score, and (iv) a deviation of the prospective coverage score and the threshold coverage score.

At step/operation 402, the predictive data analysis computing entity 106 generates a current coverage score for the observation period that is associated with the n predictive input events. An example of a current coverage score is a current coverage score that is determined based at least in part on a Proportion of Days (PDC) score for an observation period having n predictive input events.

In some embodiments, generating the current coverage gap score comprises: determining a current temporal unit count of uncovered temporal units within the observation period; for each hypothetical temporal unit count of one or more hypothetical temporal units counts within the observation period, determining a hypothetical current coverage deviation measure for a hypothetical current coverage score that is computed assuming h temporal units within the observation period are the hypothetical temporal unit count and the threshold coverage score; determining a boundary hypothetical temporal unit count having a lowest non-negative hypothetical current coverage deviation measure among hypothetical current coverage deviation measures of the one or more hypothetical temporal units; and determining the current coverage gap score based at least in part on a measure deviation of the current temporal unit count and the boundary hypothetical temporal unit count. In some embodiments, the current coverage gap score describes how many temporal units can still be uncovered by any predictive input events before the current coverage score becomes lower than a threshold coverage score.

In some embodiments, a current coverage score is a value that, when having a non-null value, describes an observed ratio (i.e., a computed ratio) of an observed coverage count for n predictive input events of an observation period to an observation period count of the observation period. In some embodiments, the current coverage score for an observation period either has a null value or a non-null value. A null current coverage score may be determined when either of the following two conditions are satisfied: (i) a dual-event entity categorization indicator for a predictive entity that is associated with the observation period is a negative dual-event entity categorization indicator, or (ii) an observation exclusion indicator for a predictive entity that is associated with the observation period is an affirmative observation exclusion indicator. A non-null current coverage score may be determined when both of the following two conditions are satisfied: (i) a dual-event entity categorization indicator for a predictive entity that is associated with the observation period is an affirmative dual-event entity categorization indicator, and (ii) an observation exclusion indicator for a predictive entity that is associated with the observation period is a negative observation exclusion indicator. In some embodiments, the non-null current coverage score for an observation period is determined based at least in part on a PDC score for the observation period.

The dual-event entity categorization indicator may describe whether an event count for a particular observation period for a particular predictive entity satisfies a current computation threshold (e.g., exceeds a current computation threshold value, such as a current computation threshold value of one). In some embodiments, when the event count for a particular observation period (i.e., the number of predictive input events in the particular observation period) satisfies the current computation threshold, the dual-event entity categorization indicator for the observation period is an affirmative dual-event entity categorization indicator. In some embodiments, when the event count for a particular observation period fails to satisfy the current computation threshold, then the dual-event entity categorization indicator for the observation event is a negative dual-event entity categorization indicator. For example, given system configuration data defining that the dual-event entity categorization indicator for a given observation period is an affirmative dual-event entity categorization indicator if the event count for the given observation period exceeds one (i.e., is two or more), then given an observation period having an event count of three (e.g., the observation period 501 that is associated with three predictive input events 511-513), then the dual-event entity categorization indicator for the noted observation period may be an affirmative dual-event entity categorization indicator. As another example, given system configuration data defining that the dual-event entity categorization indicator for a given observation period is an affirmative dual-event entity categorization indicator if the event count for the given observation period exceeds one (i.e., is two or more), then given an observation period having an event count of one (e.g., having only one predictive input events in the observation period), then the dual-event entity categorization indicator for the noted observation period may be a negative dual-event entity categorization indicator. In some embodiments, the current computation threshold value is set to one, as Center for Medicare Services (CMS) guidelines requires at least two prescription fill events before calculating a PDC score for a member/patient.

The observation exclusion indicator may describe whether a predictive entity satisfies at least one observation exclusion condition. In some embodiments, if the predictive entity satisfies at least one observation exclusion condition, the observation exclusion indicator for the predictive entity is an affirmative observation exclusion indicator. In some embodiments, if the predictive entity does not satisfy any observation exclusion conditions, the observation exclusion indicator for the predictive entity is a negative observation exclusion indicator. Operational examples of observation exclusion conditions include conditions defined by CMS for medication adherence (e.g., PDC) observation.

The observed coverage count may describe a computed number of temporal units (e.g., days) within an observation period that are covered by the n predictive input events of the observation period. In some embodiments, the observed coverage count is determined using the following operation: (i) for each of the n predictive input events of the observation period, determining a per-event coverage period that starts with the event time for the predictive input event and goes on for a number of successive temporal units that fall within a post-event period after the predictive input event whose duration is determined based at least in part on the expected cross-event temporal gap measure for the predictive input event, and (ii) computing the observed coverage count based at least in part on the number of temporal units within the observation period that fall within one of the n per-event coverage periods for the n predictive input events. For example, if a predictive input event occurs on Jan. 1, 2021, and if the expected cross-event temporal gap measure for the predictive input event is 30, then the per-event coverage period for the predictive input event runs from Jan. 1, 2021 to Jan. 30, 2021.

In the operational example of FIG. 5, assuming that each of the predictive input events 511-513 is associated with the expected cross-event temporal gap measure of 30, the predictive input event 511 has a per-event coverage period 521 that runs from Jan. 1, 2021 to Jan. 30, 2021, the predictive input event 512 has a per-event coverage period 522 that runs from Feb. 6, 2021 to Mar. 7, 2021, and the predictive input event 513 has a per-event coverage period 523 that runs from Mar. 11, 2021 to Apr. 9, 2021. In some embodiments, because 62 days of the observation period 501 are within the three per-event coverage periods for the predictive input events 511-513, then the observed coverage count for the observation period 501 may be 62. This observed coverage count may be divided by the observation period count of the observation period that describes the total number of temporal units (e.g., days) of the observation period, which in this case may be 31+28+12=71, to determine the current coverage score for the observation period 501.

At step/operation 403, the predictive data analysis computing entity 106 determines a prospective coverage score for the predictive timeframe. An exemplary prospective coverage score may be determined based at least in part on a predicted PDC, which is a prediction about an end-of-year PDC for a particular patient/member that is determined at some point before the end of the year.

In some embodiments, a prospective coverage score is a value that, when having a non-null value, describes a prediction about what the current coverage score for an observation period that includes the entirety of a predictive timeframe will be at the end of the predictive timeframe. A null prospective coverage score may be determined when either of the following two conditions are satisfied: (i) a single-event entity categorization indicator for a predictive entity that is associated with the observation period is a negative single-event entity categorization indicator, or (ii) an observation exclusion indicator for a predictive entity that is associated with the observation period is an affirmative observation exclusion indicator. A non-null prospective score may be determined when both of the following two conditions are satisfied: (i) a single-event entity categorization indicator for a predictive entity that is associated with the observation period is an affirmative single-event entity categorization indicator, and (ii) an observation exclusion indicator for a predictive entity that is associated with the observation period is a negative observation exclusion indicator. In some embodiments, the non-null prospective coverage score for a predictive timeframe is determined based at least in part on a predicted PDC score for the predictive timeframe. In some embodiments, the prospective coverage score for a predictive timeframe is determined based at least in part on the output of a prospective coverage score determination machine learning model that is configured to comprise prospective coverage model input features associated with the predictive timeframe to generate a prospective coverage score for the predictive timeframe.

The single-event entity categorization indicator may describe whether an event count for a particular observation period for a particular predictive entity satisfies a prospective computation threshold (e.g., exceeds a prospective computation threshold value, such as a prospective computation threshold value of zero). In some embodiments, when the event count for a particular observation period satisfies the current computation threshold, then the single-event entity categorization indicator for the observation period is an affirmative single-event entity categorization indicator. In some embodiments, when the event count for a particular observation period fails to satisfy the current computation threshold, the single-event entity categorization indicator is a negative single-event entity categorization indicator. For example, given system configuration data defining that the single-event entity categorization indicator for a given observation period is an affirmative single-event entity categorization indicator if the event count for the given observation period exceeds zero (i.e., is one or more), then given an observation period having an event count of three (e.g., the observation period 501 that is associated with three predictive input events 511-513), then the single-event entity categorization indicator for the noted observation period may be an affirmative single-event entity categorization indicator. As another example, given system configuration data defining that the single-event entity categorization indicator for a given observation period is an affirmative single-event entity categorization indicator if the event count for the given observation period exceeds zero (i.e., is zero or more), then given an observation period having an event count of one (e.g., having only one predictive input events in the observation period), then the single-event entity categorization indicator for the noted observation period may be a negative single-event entity categorization indicator. In some embodiments, the current computation threshold value is set to zero, such that at least one prescription fill event should be recorded/observed before calculating a predicted end-of-year PDC score for a member/patient.

The prospective coverage score determination machine learning model may be configured to process a group of prospective coverage model input features for a predictive timeframe (e.g., comprising a plurality of event distribution feature values associated with an observation period of the predictive timeframe and one or more predictive entity feature values associated with a corresponding predictive entity) to determine a prospective coverage score for the predictive timeframe. The prospective coverage score determination machine learning model may be trained based at least in part on historical data describing historically observed coverage scores for one or more historical timeframes having time durations that are equivalent to a time duration of the predictive timeframe. For example, the training data used to train the prospective coverage score determination machine learning model may include a set of training entries, where each training entry describes a computed/observed current coverage score for a particular historical predictive timeframe at the end of the particular historical predictive timeframe. In some embodiments, the prospective coverage score determination machine learning model is generated by changing the parameters of the prospective coverage score determination machine learning model to optimize an error function that is determined based at least in part on inferred prospective coverage scores for the historical predictive timeframes and the computed/observed current coverage scores for the historical predictive timeframes.

For example, a historical predictive timeframe that is used to train a prospective coverage score determination machine learning model may describe prescription fill events of at least a period of historical annual timeframe (e.g., for a member/patient that is associated with the target prospective coverage score or for another member/patient), along with the end-of-year current coverage score (e.g., the end-of-year PDC) for the historical annual period. During training, the prospective coverage score determination machine learning model may be used to generate an inferred prospective coverage score (e.g., a predicted end-of-year PDC) for the historical annual timeframe, which then may be compared to the end-of-year current coverage score (e.g., the end-of-year PDC) for the historical annual period to generate an error function. The parameters of the prospective coverage score determination machine learning model may then be updated to optimize the generated error function (e.g., by using gradient descent with or without backpropagation depending on the architecture of the regression layer of the prospective coverage score determination machine learning model).

An operational example of a prospective coverage score determination machine learning model 600 is depicted in FIG. 6. As depicted in FIG. 6, the prospective coverage score determination machine learning model 600 comprises an input filtering layer 601, a feature extraction layer 602, and a regression layer 603.

The input filtering layer 601 of the prospective coverage score determination machine learning model 600 may be configured to: determine an observation exclusion indicator for the predictive entity that is associated with an input predictive timeframe based at least in part on whether the predictive entity satisfies at least one observation exclusion condition, determine a single-event entity categorization indicator for the observation period that describes whether an event count for the one or more predictive input events satisfies a prospective computation threshold, determine that the prospective coverage score is a null prospective coverage score in response to determining that the observation exclusion indicator is an affirmative observation exclusion indicator or that the single-event entity categorization indicator is a negative single-event entity categorization indicator, and transmit a feature extraction request 610 to the feature extraction layer 602 of the prospective coverage score determination machine learning model 600 to generate prospective coverage model input features 611 in response to determining that the observation exclusion indicator is an affirmative observation exclusion indicator and that the single-event entity categorization indicator is an affirmative single-event entity categorization indicator.

As further depicted in FIG. 6, the feature extraction layer 602 of the prospective coverage score determination machine learning model 600 may be configured to, in response to receiving the feature extraction request 610 for an input predictive timeframe from the input filtering layer 601, generate prospective coverage model input features 611 for the input predictive timeframe. Examples of prospective coverage model input features 611 for a predictive timeframe include event distribution feature values for the predictive input events in the predictive timeframe, predictive entity feature values associated with the predictive entity of the predictive timeframe, and the expected cross-event temporal gap measures for the predictive input events in the predictive timeframe. For example, when the prospective coverage score determination machine learning model 600 is configured to generate a medication adherence classification for a patient/member, the predictive entity feature values may include patient demographic values. As another example, when the prospective coverage score determination machine learning model 600 is configured to generate a medication adherence classification for a patient/member, the expected cross-event temporal gap measures may describe refill periods of the prescription fill events associated with the patient/member.

In some embodiments, an event distribution feature value describes a property of a predictive timeframe that is determined based at least in part on an assumed occurrence of predictive input events during the post-observation period of the predictive timeframe. As noted above, the predictive timeframe may include an observation period that is associated with a set of observed/recorded predictive input events and a post-observation period that is not associated with any observed/recorded predictive input events. In some embodiments, an event distribution feature value describes a property of the predictive timeframe that is determined based at least in part on the set of observed/recorded predictive input events associated with the observation period of the predictive timeframe and an assumed set of predictive input events during the post-observation period of the predictive timeframe. For example, a particular event distribution feature value (referred to herein as a minimal prospective coverage score) may describe an expected current coverage score of the predictive timeframe that is determined at the end of the predictive timeframe, where the expected current coverage score is determined based at least in part on the set of observed/recorded predictive input events associated with the observation period of the predictive timeframe and an assumed empty set of predictive input events during the post-observation period of the predictive timeframe. As another example, a particular event distribution feature value (referred to herein as a maximal prospective coverage score) may describe an expected current coverage score of the predictive timeframe that is determined at the end of the predictive timeframe, where the expected current coverage score is determined based at least in part on the set of observed/recorded predictive input events associated with the observation period of the predictive timeframe and an assumed set of predictive input events during the post-observation period of the predictive timeframe that ensure that all of the temporal units of the post-observation period of the predictive timeframe are covered by an assumed predictive input event.

In some embodiments, a minimal coverage score is an event distribution feature value that describes a predicted minimal coverage score for the predictive timeframe assuming minimal event coverage during a post-observation period of the predictive timeframe. In other words, the minimal coverage score may describe an expected current coverage score for the predictive timeframe that is determined by assuming that none of the temporal units in the post-observation period of the predictive timeframe is covered by any predictive input events. In some embodiments, given a predictive timeframe that includes $d_1$ temporal units in the observation period and $d_2$ in the post-observation period, where the $d_3$ days of the observation period are covered by recorded/observed predictive input events, the minimal coverage score for the predictive timeframe is determined based at least in part on (e.g., based at least in part on a computed ratio of) a minimal coverage count that is determined based at least in part on $d_3+0$ and an observation period count that is determined based at least in part on $d_1+d_2$.

In some embodiments, a maximal coverage score is an event distribution feature value that describes a predicted maximal coverage score for the predictive timeframe assuming maximal event coverage during a post-observation period of the predictive timeframe. In other words, the maximal coverage score may describe an expected current coverage score for the predictive timeframe that is determined by assuming that all of the temporal units in the post-observation period of the predictive timeframe are covered by predictive input events. In some embodiments, given a predictive timeframe that includes $d_1$ temporal units in the observation period and $d_2$ in the post-observation period, where the $d_3$ days of the observation period are covered by recorded/observed predictive input events, the maximal coverage score for the predictive timeframe is determined based at least in part on (e.g., based at least in part on a computed ratio of) a minimal coverage count that is determined based at least in part on $d_3+d_2$ and an observation period count that is determined based at least in part on $d_1+d_2$.

As further depicted in FIG. 6, the regression layer 603 of the prospective coverage score determination machine learning model 600 may be configured to process the prospective coverage model input features 611 for an input predictive timeframe to generate the prospective coverage score 612 for the input predictive timeframe. In some embodiments, the regression layer 603 comprises a set of neural network layers (e.g., a set of fully connected neural network layers) that are configured to process the prospective coverage model input features 611 for an input predictive timeframe to generate the prospective coverage score 612 for the input predictive timeframe. In some embodiments, the regression layer 603 is trained based at least in part on one or more historically observed coverage scores for one or more historical timeframes having time durations that are equivalent to a time duration of the predictive timeframe.

Returning to FIG. 4, at step/operation 404, the predictive data analysis computing entity 106 generates a current coverage gap score for the predictive timeframe. In some embodiments, the predictive data analysis computing entity determines the current coverage gap score based at least in part on a current coverage deviation measure for (e.g., a measure of deviation of) an end-of-timeframe current coverage score and a threshold coverage score. An example of a current coverage gap score is a computed mid-year Allowable Days Remaining (ADR) for medication adherence computation for a predictive timeframe of one year that is determined based at least in part on a computed mid-year PDC measure for the particular predictive timeframe.

In some embodiments, given a predictive timeframe having d temporal units and an observation period having an observed coverage count describing u temporal units of the observation period that are uncovered (i.e., where an uncovered temporal unit does not comprise any event times for any predictive input events of the observation period), the current coverage gap score for the predictive timeframe may be determined based on a measure of deviation of: (i) a non-zero integer value of b that causes the ratio $$\left(\frac{d-b}{d} - t\right)$$

to have its smallest non-zero value (where t is a threshold coverage score), and (ii) u. In other words, In some embodiments, a current coverage gap score describes, when having a non-null value, a measure of deviation between an end-of-timeframe current coverage score for a predictive timeframe assuming all post-observation periods temporal units are covered and a threshold coverage score. An example of a threshold coverage score is an 0.80 threshold coverage score (e.g., a threshold PDC measure of 80% as defined by CMS). For example, in some embodiments, a non-null current coverage describes a maximum number of temporal units (e.g., days) within a post-observation period of the predictive timeframe that can be uncovered by any predictive input events (e.g., prescription fill events) before the current coverage score for the predictive timeframe falls below the threshold coverage score. Accordingly, in some embodiments, a non-null current coverage score describes a largest discrete value for a computed number of uncovered temporal units in the post-observation period of the predictive timeframe that can nevertheless lead to a positive current coverage deviation measure for the current coverage score and a threshold coverage score. Because of the negative relationship between the number of uncovered temporal units in a period and the current coverage score of that period, at some point an increasing number of uncovered temporal units will cause the current coverage score to go below the threshold coverage score. In some embodiments, the current coverage gap score describes the discrete value for the number of uncovered temporal units in the period that will cause the measure of deviation between the current coverage score for the period and the threshold coverage score to attain its minimal non-negative value. Naturally, this measure depends on the value of the current coverage score, which in turn may depend on the number of temporal units in the period that are covered by predictive input events. In some embodiments, when the current coverage score has a null value, the current coverage gap score also has a null value.

At step/operation 405, the predictive data analysis computing entity 106 generates a prospective coverage gap score for the predictive timeframe based at least in part on a prospective coverage deviation measure for (e.g., a measure of deviation of) the prospective coverage score and the threshold coverage score. An example of a current coverage gap score is a predicted year-end Allowable Days Remaining (ADR) for medication adherence computation at the end of a predictive timeframe of one year that is determined based at least in part on the predicted year-end PDC measure for the particular predictive timeframe.

In some embodiments, a prospective coverage gap score describes, when having a non-null value, a measure of deviation between a current prospective score for a predictive timeframe and a threshold coverage score. As described above, an example of a threshold coverage score is an 0.80 threshold coverage score (e.g., a threshold PDC measure of 80% as defined by CMS). For example, the prospective coverage gap score for a predictive timeframe may describe, assuming a particular prospective coverage score for the predictive timeframe that describes a predicted end-of-timeframe (e.g., year-end) current coverage score for the predictive timeframe, a measure of deviation between: (i) a first number of temporal units (e.g., days) in the predictive timeframe that are predicted to not be covered by any predictive input events under the assumption that the end-of-timeframe (e.g., year-end) current coverage score for the predictive timeframe indeed equals the particular prospective coverage score, and (ii) a second number of temporal units (e.g., days) in the predictive timeframe that, when covered by predictive input events, cause prospective coverage deviation measure to have its largest negative value. In some embodiments, the first number noted above is generated based at least in part on a*b, where a is the predictive coverage score for the predictive timeframe and b is the total number of days (i.e., the predictive timeframe count) of the predictive timeframe. In some embodiments, the second number noted above is the largest value of t such that (t/b)<0, where t is an assumed number of covered temporal units in the predictive timeframe and b is the total number of days (i.e., the predictive timeframe count) of the predictive timeframe. In some embodiments, when the prospective coverage score has a null value, the prospective coverage gap score also has a null value.

At step/operation 406, the predictive data analysis computing entity 106 generates the prospective event-based classification for the predictive entity based at least in part on a group of classification input features comprising the current coverage score, the prospective coverage score, the current coverage gap score, and the prospective coverage score. In some embodiments, the predictive data analysis computing entity 106 generates the prospective event-based classification using a prospective event-based classification machine learning model, where the prospective event-based classification machine learning model is configured to map the predictive entity to a selected classification of a plurality of defined classifications based at least in part on a group of classification input features comprising the current coverage score, the prospective coverage score, the current coverage gap score, and the prospective coverage score.

In some embodiments, the prospective event-based classification describes a predicted designation for a predictive entity (e.g., for a patient/member) in the totality of a predictive timeframe that is determined based at least in part on predictive input events observed/recorded during only a portion (i.e., an observation period) of the noted predictive timeframe. An example of a prospective event-based classification is a medication adherence classification for a patient/member during a year that is determined based at least in part on observed/recorded medication fill events of the patient/member during only a portion of the year. In some embodiments, the prospective event-based classification is event-based because the prospective event-based classification is determined based at least in part on predictive input events that occur within the predictive timeframe and in relation to the predictive entity and the event category. In some embodiments, the prospective event-based classification is prospective because the prospective event-based classification is determined based at least in part on predictive input events associated with only a portion of the predictive timeframe (i.e., the observation period of the predictive timeframe, while excluding the post-observation period of the predictive timeframe).

In some embodiments, the prospective event-based classification machine learning model is a machine learning model that is configured to process a group of classification input features for a predictive entity to determine a prospective event-based classification for the predictive entity. In some embodiments, the prospective event-based classification machine learning model maps a predictive entity to a selected prospective event-based classification of a set of candidate prospective event-based classifications. To do so, the prospective event-based classification machine learning model may use one or more classification engines. For example, in some embodiments, the prospective event-based classification machine learning model may use m classification engines each having a learned/trained/predefined engine weight to generate m per-engine selected prospective event-based classifications for a predictive entity, then generate a classification score for each candidate prospective event-based classification based learned/trained/predefined engine weights of a subset of the m classification engine that have recommended the candidate prospective event-based classification as their respective per-engine selected prospective event-based classifications, and then select a candidate prospective event-based classification having a highest classification score as the prospective event-based classification for the predictive entity. As another example, the prospective event-based classification machine learning model may use m classification engines each having a learned/trained/predefined engine weight to generate m per-engine selected prospective event-based classifications for a predictive entity, then generate a classification score for each candidate prospective event-based classification based learned/trained/predefined engine weights of a subset of the m classification engine that have recommended the candidate prospective event-based classification as their respective per-engine selected prospective event-based classifications, and then select a subset of candidate prospective event-based classifications having a threshold-satisfying classification score as the prospective event-based classifications for the predictive entity.

Examples of classification engines that can be used by a prospective event-based classification machine learning model include rule-based classification engines, feedforward neural network classification engines, clustering classification engines, and recurrent neural network engines. In some embodiments, a rule-based classification engine is configured to recommend a selected prospective event-based classification for a predictive entity based at least in part on whether a group of classification input features for the predictive entity satisfy one or more of a set of classification rules. Examples of classification rules include at least one of the below numerated classification rules, where an operational example of each numerated classification rule is provided in FIG. 7 via a co-numbered medication adherence classification rule:

(1) A classification rule describing that a predictive entity having a non-null prospective coverage score, having an affirmative initiation indicator with respect to the target event category (e.g., the target medication/therapy) that has less than two predictive input events in the observation period of an analyzed predictive timeframe and a prospective coverage gap score that satisfies (e.g., falls above or equals) a safety prospective coverage gap score threshold (e.g., a safety prospective coverage gap score threshold of ten) is associated with an initiation prospective event-based classification;

(2) A classification rule describing that a predictive entity having a non-null current coverage score having a current coverage gap score that falls within an urgency current coverage gap score region (e.g., an urgency current coverage gap score region of [0, 7]) is associated with a urgent attention prospective event-based classification;

(3) A classification rule describing that a predictive entity whose observation period endpoint is more than U (e.g., 29) temporal units falls after a period of O temporal units subsequent to the event time for the latest predictive input event (where O may be determined based at least in part on the expected cross-event temporal gap measure for the latest predictive input event), whose the current coverage gap score for the predictive entity is non-negative, and whose current coverage gap score is non-null is associated with a singular delayed action prospective event-based classification;

(4) A classification rule describing that a predictive entity whose observation period endpoint is after a period of O temporal units subsequent to the event time for the latest predictive input event (where O may be determined based at least in part on the expected cross-event temporal gap measure for the latest predictive input event), whose prospective coverage score fails to satisfy (e.g., falls below) a heightened threshold coverage score (e.g., 0.90), whose current coverage score is non-null, who is associated with at least one temporal unit that falls after $e_i$ and is not covered by any predictive input events and at least one temporal unit that falls after $e_{i-1}$ and is not covered by any predictive input events (where $e_i$ is the latest predictive input event in the analyzed predictive timeframe of the predictive entity and $e_{i-1}$ is the predictive input event immediately before $e_i$ fin the analyzed predictive timeframe of the predictive entity), whose maximum allowed cross-event temporal gap measure (e.g., maximum refill date) for $e_i$ is non-negative, and whose current coverage gap score is non-negative is associated with a double delayed action prospective event-based classification;

(5) A classification rule describing that a predictive entity whose observation period endpoint is after a period of O temporal units subsequent to the event time for the latest predictive input event (where O may be determined based at least in part on the expected cross-event temporal gap measure for the latest predictive input event), and whose prospective coverage score fails to satisfy (e.g., falls below) a heightened threshold coverage score (e.g., 0.90) is associated with an ordinary delayed action prospective event-based classification if either the current coverage gap score for the predictive entity is non-negative or the prospective coverage gap score for the predictive entity satisfies (e.g., falls above or equals) a safety prospective coverage gap score threshold (e.g., a safety prospective coverage gap score threshold of ten);

(6) A classification rule describing that a predictive entity whose current coverage score is within a medial current coverage score region (e.g., a medical current coverage score region of [0.40, 0.60], whose current coverage gap score is non-negative is associated with an instruction error prospective event-based classification if, for each $e_i$ of the last s (e.g., two) predictive input events in the predictive timeframe of the predictive entity, the number of temporal units between the event date for $e_i$ and the terminal endpoint of the event coverage period for preceding predictive input event $e_{i-1}$ in the predictive timeframe of the predictive entity is within a defined delay region (e.g., a defined delay region of [40, 60];

(7) A classification rule describing that a predictive entity whose prospective coverage score is non-null is associated with a temporal gap widening prospective event-based classification if: (i) either the current coverage score for the predictive entity is non-negative or the prospective coverage gap score for the predictive entity satisfies (e.g., falls above or equals) a safety prospective coverage gap score threshold (e.g., a safety prospective coverage gap score threshold of ten), and (ii) the expected cross-event temporal gap measure for the latest predictive input event associated with the predictive entity satisfies (e.g., falls below) a lower gap threshold (e.g., a lower gap threshold of seventy);

(8) A classification rule describing that a predictive entity whose prospective coverage score is non-null is associated with a heightened temporal gap widening prospective event-based classification if: (i) either the current coverage score for the predictive entity is non-negative or the prospective coverage gap score for the predictive entity satisfies (e.g., falls above or equals) a safety prospective coverage gap score threshold (e.g., a safety prospective coverage gap score threshold of ten), and (ii) the expected cross-event temporal gap measure for the latest predictive input event associated with the predictive entity satisfies (e.g., falls below) a lower gap threshold (e.g., a lower gap threshold of seventy);

(9) A classification rule describing that a predictive entity whose prospective coverage score is non-null is associated with the heightened temporal gap widening prospective event-based classification if: (i) either the current coverage score for the predictive entity is non-negative or the prospective coverage gap score for the predictive entity satisfies (e.g., falls above or equals) a safety prospective coverage gap score threshold (e.g., a safety prospective coverage gap score threshold of ten), and (ii) the expected cross-event temporal gap measure for the latest predictive input event associated with the predictive entity equals a heightened gap value (e.g., a heightened gap value of ninety);

(10) A classification rule describing that a predictive entity is associated with a time-frame-wide historical non-adherence classification if the most recently ended historical timeframe for the predictive entity is indicated as a non-adherent (e.g., "red") timeframe, and the predictive entity is associated with a number of predictive input events in a current predictive timeframe that fails to satisfy (e.g., falls below or equals) a frequency event count threshold (e.g., a frequency event count threshold of two) as well as a predicted coverage gap score that satisfies (e.g., falls above or equals) a safety prospective coverage gap score threshold (e.g., a safety prospective coverage gap score threshold of ten); and

(11) A classification rule describing that a predictive entity is associated with the time-frame-wide historical non-adherence classification if the most recently ended historical timeframe for the predictive entity is associated with an end-of-timeframe (e.g., end-of-year) current coverage score that falls below a coverage score threshold (e.g., a coverage score threshold of 0.80), and the predictive entity is associated with no predictive input events in the current predictive timeframe.

In some embodiments, a feedforward classification engine is configured to process a group of classification input features for a predictive entity using a feedforward neural network machine learning model to determine a selected prospective event-based classification for the predictive entity. In some embodiments, the feedforward (e.g., fully connected) neural network machine learning model is trained using training data that is generated by mapping historical action recommendation designation codes for particular predictive entities (e.g., historical pharmacist-provided action recommendation designation codes for particular members/patients, historical physician-provided action recommendation designation codes for particular members/patients, and/or the like) to corresponding candidate prospective event-based classifications, and then use each mapped candidate prospective event-based classification as a ground-truth classification label for the predictive entity that is associated with the particular predictive entity. Accordingly, in some embodiments, each training entry used to train the feedforward neural network machine learning model comprises: (i) one or more training input fields determined based at least in part on the group of classification input features for a corresponding predictive entity, and (ii) one or more ground-truth classification labels for the corresponding predictive entity generated based at least in part on candidate prospective event-based classifications mapped to historical action recommendation designation codes for the corresponding predictive entity. During training, the feedforward neural network machine learning model may be used to generate an inferred classification score vector for each training entry that describes an inferred classification score for the training entry with respect to each of the candidate prospective event-based classifications. Afterward, a training engine may generate an error function based at least in part on a deviation of the inferred classification score vector and a ground-truth classification score vector for the training entry that is determined based at least in part on the ground-truth classification labels for the corresponding predictive entity (e.g., a vector that has "1" values in locations corresponding to candidate prospective event-based classifications associated with the ground-truth classification labels and has "0" values in other locations). The parameters of the feedforward neural network machine learning model may then be updated to optimize the generated error function (e.g., by using gradient descent with backpropagation).

In some embodiments, the clustering classification engine is configured to map a set of E predictive entities to a multi-dimensional classification space characterized by feature dimensions that are associated with the feature types of the classification input features for each predictive entity. Afterward, the predictive data analysis computing entity 106 may apply a clustering routine (e.g., a k-means clustering routine) to the multi-dimensional classification space to generate C inferred classifications. Then, the clustering classification engine is configured to identify the inferred classification that is associated with an input predictive entity and then map the inferred classification to one or more of the defined candidate prospective event-based classifications. For example, in some embodiments, the clustering classification engine may generate a set of inferred classification feature values for the inferred classification that is associated with an input predictive entity, provide the inferred classification feature values to a classification mapping machine learning model, and determine a mapping of the inferred classification based at least in part on the output of the classification mapping machine learning model. In some embodiments, the classification mapping machine learning model is a feedforward (e.g., fully connected) neural network machine learning model that is configured to map a classification mapping score for each of the defined candidate prospective event-based classifications, with the input inferred classification being mapped to either the candidate prospective event-based classification having a highest classification mapping score or to each candidate prospective event-based classification having a threshold-satisfying classification mapping score. In some embodiments, inferred classification feature values of an input inferred classification include: (i) one or more feature values each describing a statistical distribution measure (e.g., mean, weighted geometric mean as adjusted by weights determined based at least in part on distances to a geometric centroid of the inferred cluster, median, and/or the like) of the current coverage scores for the predictive entities in the inferred cluster, (ii) one or more feature values each describing a statistical distribution measure (e.g., mean, weighted geometric mean as adjusted by weights determined based at least in part on distances to a geometric centroid of the inferred cluster, median, and/or the like) of the prospective coverage scores for the predictive entities in the inferred cluster, (iii) one or more feature values each describing a statistical distribution measure (e.g., mean, weighted geometric mean as adjusted by weights determined based at least in part on distances to a geometric centroid of the inferred cluster, median, and/or the like) of the current coverage gap scores for the predictive entities in the inferred cluster, and/or (iv) one or more feature values each describing a statistical distribution measure (e.g., mean, weighted geometric mean as adjusted by weights determined based at least in part on distances to a geometric centroid of the inferred cluster, median, and/or the like) of the prospective coverage gap scores for the predictive entities in the inferred cluster.

In some embodiments, the recurrent neural network classification engine is configured to, at each current timestep that is associated with a current timestamp of an event time of a latest prediction input event, process a group of classification input features for a predictive entity as determined using an observation period ending in the current timestamp as well as an input hidden state vector using a recurrent (e.g., long short term memory) neural network machine learning model to determine an updated hidden state vector. In some embodiments, the input hidden state vector to the initial timestep is a default hidden state vector (e.g., an all zero hidden state vector), while the input hidden state vector to each post-initial timestep is the updated timestep vector an immediately preceding timestep. In some embodiments, at each time, the updated hidden state vector for a latest timestep is processed using a set of discriminant layers to generate a classification score vector.

In some embodiments, the recurrent neural network machine learning model is trained using training data that is generated by mapping historical action recommendation designation codes for particular predictive entities (e.g., historical pharmacist-provided action recommendation designation codes for particular members/patients, historical physician-provided action recommendation designation codes for particular members/patients, and/or the like) to corresponding candidate prospective event-based classifications, and then use each mapped candidate prospective event-based classification as a ground-truth classification label for the predictive entity that is associated with the particular predictive entity. Accordingly, in some embodiments, each training entry used to train the recurrent neural network machine learning model comprises: (i) one or more training input fields determined based at least in part on the group of classification input features for a corresponding predictive entity, and (ii) one or more ground-truth classification labels for the corresponding predictive entity generated based at least in part on candidate prospective event-based classifications mapped to historical action recommendation designation codes for the corresponding predictive entity. During training, the recurrent neural network machine learning model may be used to generate an inferred classification score vector for each training entry that describes an inferred classification score for the training entry with respect to each of the candidate prospective event-based classifications. Afterward, a training engine may generate an error function based at least in part on a deviation of the inferred classification score vector and a ground-truth classification score vector for the training entry that is determined based at least in part on the ground-truth classification labels for the corresponding predictive entity (e.g., a vector that has "1" values in locations corresponding to candidate prospective event-based classifications associated with the ground-truth classification labels and has "0" values in other locations). The parameters of the recurrent neural network machine learning model may then be updated to optimize the generated error function (e.g., by using gradient descent with backpropagation through time).

At step/operation 407, the predictive data analysis computing entity 106 performs one or more prediction-based actions based at least in part on the prospective event-based classification for the predictive entity. In some embodiments, each candidate prospective event-based classification is associated with a set of prediction-based actions, and the one or more prediction-based actions described herein comprise the set of prediction-based actions for the prospective event-based classification (or for any of one or more prospective event-based classifications that are deemed to be associated with the predictive entity).

In some embodiments, performing the prediction-based actions comprises generating user interface data for a recommendation user interface that displays a recommendation message associated with the prospective event-based classification for the predictive entity. Operational examples of such recommendation messages 702 are described in the recommendation message configuration data table 700 of FIG. 7. As depicted in FIG. 7, each numerated row of the recommendation message configuration data table 700 of FIG. 7 corresponds to a classification rule 701 that is an example of a co-numbered classification rule of the eleven numerated classification rules described above with respect to an exemplary classification engine of a prospective event-based classification machine learning model. For example, classification rule (1) of FIG. 7 is an example of classification rule (1) described above, classification rule (2) of FIG. 7 is an example of classification rule (2) described above, and so on. As further depicted in FIG. 7, each classification rule is associated with a recommendation message 702 and a recommendation logic 703.

For example, classification rule (1) of FIG. 7 maps a patient/member (which is an example of a predictive entity) to an initiation prospective event-based classification if the patient/member has a non-null EOY PDC (i.e., an end-of-year predicted PDC, which is an example of a prospective coverage period), meets the new therapy logic requirements for a particular therapy/medication (and thus has an affirmative initiation indicator with respect to a target event category), has less than two prescription fill events in a current year (and thus has less than two predictive input events in the observation period of an analyzed predictive timeframe), and has a PM_ADR (i.e., a predicted end-of-year ADR) that falls above or equals a safety prospective coverage gap score threshold of ten. In some embodiments, if a patient/member satisfies classification rule (1), the patient/member is mapped to a recommendation message of "counsel on new medication" with the described recommendation logic.

An operational example of a recommendation user interface 800 is depicted in FIG. 8. As depicted in FIG. 8, the recommendation user interface 800 includes a Gaps In Care tab 801 that describes, for a particular patient/member described by the patient information panel 811, recommendation messages 821-823 for three separate medications. In the operational example of FIG. 8, each medication of the three medications is assigned to an instruction error prospective event-based classification, and thus assigned to a temporal gap widening prospective event-based classification and thus assigned a "Consider 3-month supply" recommendation message. As further depicted in FIG. 8, each recommendation message is associated with a "More Info"

button, where user interaction with the "More Info" button for a recommendation message displays metadata information for the medication/prescription associated with the corresponding medication.

Examples of a prediction-based action for a prospective event-based classification include a prediction-based actions that comprises at least one of: (i) generating a user interface that displays recommendation messages for particular event categories (e.g., particular medication types) in relation to a particular predictive entity (e.g., a particular patient/member), (ii) automatically scheduling provider appointments for a predictive entity in response to determining that the prospective event-based classification for the predictive entity in relation to an event category is associated with a prediction-based action that requires provider appointments for predictive entities associated with the prospective event-based classification, (iii) automatically generating prescriptions and/or other service requests for a predictive entity in response to determining that the prospective event-based classification for the predictive entity in relation to an event category is associated with a prediction-based action that requires prescriptions and/or other service requests for predictive entities associated with the prospective event-based classification, and (iv) performing operational load balancing operations for server systems of an online pharmacy platform based at least in part on recommended messages of particular patients/members.

Accordingly, as described above, to address the obstacles associated with performing machine learning tasks such as classification using discrete timeseries-based forecasts, various embodiments of the present invention utilize machine learning models that perform prospective event-based classification based on features extracted based only on the observation period of a predictive timeframe as well as features extracted by assuming trends of the observation period continue in the post-observation period. The noted solutions thus introduce computationally efficient methods for performing simultaneous timeseries-based forecasts using discrete timeseries data and using the forecast data along with observation data to perform classification tasks. In some embodiments, only a prospective coverage score is forecasted using a machine learning model, and all other feature values are linearly derived based on observation data and/or based on computed forecast data. By using the above-noted techniques, various embodiments of the prevent invention address technical challenges associated with performing machine learning tasks such as classification using discrete timeseries-based forecasts and reduce computational/storage load on predictive data analysis systems that are configured to perform machine learning tasks such as classification using discrete timeseries-based forecasts.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:
1. A computer-implemented method comprising:
   generating, by one or more processors and based at least in part on one or more predictive input events occurring during an observation period of a predictive timeframe associated with a predictive entity, a current coverage score for the observation period;
   generating, by the one or more processors executing a prospective coverage score determination machine learning model comprising one or more neural network layers and trained based at least in part on historically observed coverage scores for one or more historical timeframes, a prospective coverage score for the predictive timeframe based at least in part on a group of prospective coverage model input features comprising an event distribution feature value associated with the one or more predictive input events and a predictive entity feature value associated with the predictive entity;
   generating, by the one or more processors and based at least in part on a prospective coverage deviation measure for the prospective coverage score and a threshold coverage measure, a prospective coverage gap score for the predictive timeframe;
   inputting, by the one or more processors and into a prospective event-based classification machine learning model, the current coverage score, the prospective coverage score, and the prospective coverage gap score as a group of classification input features, causing the prospective event-based classification machine learning model to generate a prospective event-based classification that is indicative of a prospective outcome associated with the predictive entity for the predictive timeframe, wherein the prospective event-based classification machine learning model is trained using a training set comprising a plurality of training entries each having a classification label; and
   performing, by the one or more processors, one or more prediction-based actions based at least in part on the prospective event-based classification.

2. The computer-implemented method of claim 1, wherein generating the current coverage score comprises:
   determining a dual-event entity categorization indicator for the observation period that describes whether an event count for the one or more predictive input events satisfies a current computation threshold,
   determining an observation exclusion indicator for the predictive entity based at least in part on whether the predictive entity satisfies at least one observation exclusion condition; and
   in response to determining that the dual-event entity categorization indicator is a negative dual-event entity categorization indicator or that the observation exclusion indicator is an affirmative observation exclusion indicator, generating a null current coverage score.

3. The computer-implemented method of claim 1, wherein generating the current coverage score comprises:
   determining a dual-event entity categorization indicator for the observation period that describes whether an event count for the one or more predictive input events satisfies a current computation threshold,
   determining an observation exclusion indicator for the predictive entity based at least in part on whether the predictive entity satisfies at least one observation exclusion condition; and
   in response to determining that the dual-event entity categorization indicator is an affirmative dual-event entity categorization indicator and the observation exclusion indicator is a negative observation exclusion indicator, determining the current coverage score based at least in part on an observed ratio of an observed coverage count for the one or more predictive input events to an observation period count of the observation period.

4. The computer-implemented method of claim 1, wherein the prospective coverage score determination machine learning model comprises an input filtering neural network layer for:
   determining an observation exclusion indicator for the predictive entity based at least in part on whether the predictive entity satisfies at least one observation exclusion condition,
   determining a single-event entity categorization indicator for the observation period that describes whether an event count for the one or more predictive input events satisfies a prospective computation threshold,
   determining that the prospective coverage score is a null prospective coverage score in response to determining that the observation exclusion indicator is an affirmative observation exclusion indicator or that the single-event entity categorization indicator is a negative single-event entity categorization indicator, and
   causing a feature extraction neural network layer of the prospective coverage score determination machine learning model to generate the group of prospective coverage model input features in response to determining that the observation exclusion indicator is the affirmative observation exclusion indicator and that the single-event entity categorization indicator is an affirmative single-event entity categorization indicator.

5. The computer-implemented method of claim 1, wherein:
   the prospective coverage score determination machine learning model comprises a regression neural network layer that is configured to determine the prospective coverage score based at least in part on the group of prospective coverage model input features, and
   the regression neural network layer is trained based at least in part on one or more historically observed coverage scores for one or more historical timeframes having time durations that are equivalent to a time duration of the predictive timeframe.

6. The computer-implemented method of claim 1, wherein the group of prospective coverage model input features further comprise an expected cross-event temporal gap measure for the predictive timeframe.

7. The computer-implemented method of claim 6, wherein the group of classification input features comprise the expected cross-event temporal gap measure.

8. The computer-implemented method of claim 1, wherein:
   the event distribution feature value comprises a minimal prospective coverage score and a maximal prospective coverage score,
   the minimal prospective coverage score reflects a predicted minimal coverage score for the predictive timeframe for minimal event coverage during a post-observation period of the predictive timeframe, and
   the maximal prospective coverage score reflects a predicted maximal coverage score for the predictive timeframe for maximal event coverage during the post-observation period of the predictive timeframe.

9. A system comprising at least one processor and memory including program code, the memory and the program code configured to, with the at least one processor, cause the apparatus to at least:
   generate, based at least in part on one or more predictive input events occurring during an observation period of a predictive timeframe associated with a predictive entity, a current coverage score for the observation period;
   generate a prospective coverage score for the predictive timeframe using a prospective coverage score determination machine learning model comprising one or more neural network layers and trained based at least in part on historically observed coverage scores for one or more historical timeframes, based at least in part on a group of prospective coverage model input features comprising an event distribution feature value associated with the one or more predictive input events and a predictive entity feature value associated with the predictive entity;
   generate, based at least in part on a prospective coverage deviation measure for the prospective coverage score and a threshold coverage measure, a prospective coverage gap score for the predictive timeframe;
   input into a prospective event-based classification machine learning model, the current coverage score, the prospective coverage score, and the prospective coverage gap score as a group of classification input features, causing the prospective event-based classification machine learning model to generate a prospective event-based classification that is indicative of a prospective outcome associated with the predictive entity for the predictive timeframe, wherein the prospective event-based classification machine learning model is trained using a training set comprising a plurality of training entries each having a classification label; and
   perform one or more prediction-based actions based at least in part on the prospective event-based classification.

10. The system of claim 9, wherein to generate the current coverage score, the memory and the program code configured to, with the at least one processor, further cause the apparatus to:
   determine a dual-event entity categorization indicator for the observation period that describes whether an event count for the one or more predictive input events satisfies a current computation threshold,
   determine an observation exclusion indicator for the predictive entity based at least in part on whether the predictive entity satisfies at least one observation exclusion condition; and
   in response to a determination that the dual-event entity categorization indicator is a negative dual-event entity categorization indicator or that the observation exclusion indicator is an affirmative observation exclusion indicator, generate a null current coverage score.

11. The system of claim 9, wherein to generate the current coverage score, the memory and the program code configured to, with the at least one processor, further cause the apparatus to:
   determine a dual-event entity categorization indicator for the observation period that describes whether an event count for the one or more predictive input events satisfies a current computation threshold,
   determine an observation exclusion indicator for the predictive entity based at least in part on whether the predictive entity satisfies at least one observation exclusion condition; and
   in response to a determination that the dual-event entity categorization indicator is an affirmative dual-event entity categorization indicator and the observation exclusion indicator is a negative observation exclusion indicator, determine the current coverage score based at least in part on an observed ratio of an observed coverage count for the one or more predictive input events to an observation period count of the observation period.

12. The system of claim 9, wherein the prospective coverage score determination machine learning model comprises an input filtering neural network layer that is configured to:
    determine an observation exclusion indicator for the predictive entity based at least in part on whether the predictive entity satisfies at least one observation exclusion condition,
    determine a single-event entity categorization indicator for the observation period that describes whether an event count for the one or more predictive input events satisfies a prospective computation threshold,
    determine that the prospective coverage score is a null prospective coverage score in response to a determination that the observation exclusion indicator is an affirmative observation exclusion indicator or that the single-event entity categorization indicator is a negative single-event entity categorization indicator, and
    cause a feature extraction neural network layer of the prospective coverage score determination machine learning model to generate the group of prospective coverage model input features in response to a determination that the observation exclusion indicator is the affirmative observation exclusion indicator and that the single-event entity categorization indicator is an affirmative single-event entity categorization indicator.

13. The system of claim 9, wherein:
    the prospective coverage score determination machine learning model comprises a regression neural network layer that is configured to determine the prospective coverage score based at least in part on the group of prospective coverage model input features, and
    the regression neural network layer is trained based at least in part on one or more historically observed coverage scores for one or more historical timeframes having time durations that are equivalent to a time duration of the predictive timeframe.

14. The system of claim 9, wherein the group of prospective coverage model input features further comprise an expected cross-event temporal gap measure for the predictive timeframe.

15. The system of claim 14, wherein the group of classification input features comprise the expected cross-event temporal gap measure.

16. The system of claim 9, wherein:
    the event distribution feature value comprises a minimal prospective coverage score and a maximal prospective coverage score,
    the minimal prospective coverage score reflects a predicted minimal coverage score for the predictive timeframe for minimal event coverage during a post-observation period of the predictive timeframe, and
    the maximal prospective coverage score reflects a predicted maximal coverage score for the predictive timeframe for maximal event coverage during the post-observation period of the predictive timeframe.

17. One or more non-transitory computer-readable storage media including instructions that, when executed by one or more processors, cause the one or more processors to:
    generate, based at least in part on one or more predictive input events occurring during an observation period of a predictive timeframe associated with a predictive entity, a current coverage score for the observation period;
    generate a prospective coverage score for the predictive timeframe using a prospective coverage score determination machine learning model comprising one or more neural network layers and trained based at least in part on historically observed coverage scores for one or more historical timeframes, based at least in part on a group of prospective coverage model input features comprising an event distribution feature value associated with the one or more predictive input events and a predictive entity feature value associated with the predictive entity;
    generate, based at least in part on a prospective coverage deviation measure for the prospective coverage score and a threshold coverage measure, a prospective coverage gap score for the predictive timeframe;
    input into a prospective event-based classification machine learning model, the current coverage score, the prospective coverage score, and the prospective coverage gap score as a group of classification input features, causing the prospective event-based classification machine learning model to generate a prospective event-based classification that is indicative of a prospective outcome associated with the predictive entity for the predictive timeframe, wherein the prospective event-based classification machine learning model is trained using a training set comprising a plurality of training entries each having a classification label; and
    perform one or more prediction-based actions based at least in part on the prospective event-based classification.

18. The one or more non-transitory computer-readable storage media of claim 17, wherein to generate the current coverage score, the instructions, when executed by one or more processors, further cause the one or more processors to:
    determine a dual-event entity categorization indicator for the observation period that describes whether an event count for the one or more predictive input events satisfies a current computation threshold,
    determine an observation exclusion indicator for the predictive entity based at least in part on whether the predictive entity satisfies at least one observation exclusion condition; and
    in response to a determination that the dual-event entity categorization indicator is a negative dual-event entity categorization indicator or that the observation exclusion indicator is an affirmative observation exclusion indicator, generate a null current coverage score.

19. The one or more non-transitory computer-readable storage media of claim 17, wherein to generate the current coverage score, the instructions, when executed by one or more processors, further cause the one or more processors to:
    determine a dual-event entity categorization indicator for the observation period that describes whether an event count for the one or more predictive input events satisfies a current computation threshold,
    determine an observation exclusion indicator for the predictive entity based at least in part on whether the predictive entity satisfies at least one observation exclusion condition; and in response to a determination that the dual-event entity categorization indicator is an affirmative dual-event entity categorization indicator and the observation exclusion indicator is a negative observation exclusion indicator, determine the current coverage score based at least in part on an observed ratio of an observed coverage count for the one or more predictive input events to an observation period count of the observation period.

20. The one or more non-transitory computer-readable storage media of claim 17, wherein the prospective coverage score determination machine learning model comprises an input filtering neural network layer that is configured to:

determine an observation exclusion indicator for the predictive entity based at least in part on whether the predictive entity satisfies at least one observation exclusion condition, determine a single-event entity categorization indicator for the observation period that describes whether an event count for the one or more predictive input events satisfies a prospective computation threshold, determine that the prospective coverage score is a null prospective coverage score in response to a determination that the observation exclusion indicator is an affirmative observation exclusion indicator or that the single-event entity categorization indicator is a negative single-event entity categorization indicator, and cause a feature extraction neural network layer of the prospective coverage score determination machine learning model to generate the group of prospective coverage model input features in response to a determination that the observation exclusion indicator is the affirmative observation exclusion indicator and that the single-event entity categorization indicator is an affirmative single-event entity categorization indicator.

* * * * *